US010202658B2

(12) United States Patent
Parkin et al.

(10) Patent No.: US 10,202,658 B2
(45) Date of Patent: *Feb. 12, 2019

(54) METHODS FOR DETERMINING HYPERSUSCEPTIBILITY OF HIV-1 TO NON-NUCLEOSIDE REVERSE TRANSCRIPTASE INHIBITORS

(75) Inventors: Neil T. Parkin, Belmont, CA (US); Eoin Coakley, San Francisco, CA (US)

(73) Assignee: Monogram Biosciences, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/467,527

(22) Filed: May 9, 2012

(65) Prior Publication Data

US 2012/0283250 A1  Nov. 8, 2012

Related U.S. Application Data

(62) Division of application No. 11/884,667, filed as application No. PCT/US2006/005511 on Feb. 16, 2006, now Pat. No. 8,178,291.

(60) Provisional application No. 60/654,738, filed on Feb. 18, 2005, provisional application No. 60/685,301, filed on May 26, 2005.

(51) Int. Cl.
    C12Q 1/70          (2006.01)
(52) U.S. Cl.
    CPC ..................... C12Q 1/703 (2013.01)
(58) Field of Classification Search
    None
    See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,631,734 A | 5/1997 | Stern et al. |
| 5,723,320 A | 3/1998 | Dehlinger |
| 5,744,305 A | 4/1998 | Fodor et al. |
| 5,834,758 A | 11/1998 | Trulson et al. |
| 5,837,464 A | 11/1998 | Capon et al. |
| 5,837,832 A | 11/1998 | Chee et al. |
| 5,919,523 A | 7/1999 | Sundberg et al. |
| 6,022,963 A | 2/2000 | McGall et al. |
| 6,040,138 A | 3/2000 | Lockhart et al. |
| 6,141,096 A | 10/2000 | Stern et al. |
| 6,156,501 A | 12/2000 | McGall et al. |
| 6,168,948 B1 | 1/2001 | Anderson et al. |
| 6,197,506 B1 | 3/2001 | Fodor et al. |
| 6,225,625 B1 | 5/2001 | Pirrung et al. |
| 6,242,187 B1 | 6/2001 | Capon et al. |
| 6,261,776 B1 | 7/2001 | Pirrung et al. |
| 6,284,465 B1 | 9/2001 | Wolber |
| 6,287,850 B1 | 9/2001 | Besemer et al. |
| 6,291,183 B1 | 9/2001 | Pirrung et al. |
| 6,308,170 B1 | 10/2001 | Balaban |
| 6,309,823 B1 | 10/2001 | Cronin et al. |
| 6,333,155 B1 | 12/2001 | Lockhart et al. |
| 6,342,355 B1 | 1/2002 | Hacia et al. |
| 6,355,432 B1 | 3/2002 | Fodor et al. |
| 6,379,895 B1 | 4/2002 | Fodor et al. |
| 6,391,550 B1 | 5/2002 | Lockhart et al. |
| 6,410,229 B1 | 6/2002 | Lockhart et al. |
| 6,451,536 B1 | 9/2002 | Fodor et al. |
| 6,489,114 B2 | 12/2002 | Laayoun et al. |
| 6,505,125 B1 | 1/2003 | Ho |
| 6,548,257 B2 | 4/2003 | Lockhart et al. |
| 6,551,784 B2 | 4/2003 | Fodor et al. |
| 6,617,112 B2 | 9/2003 | Beals |
| 6,670,124 B1 | 12/2003 | Chow et al. |

FOREIGN PATENT DOCUMENTS

| | | |
|---|---|---|
| WO | WO 97/27319 | 7/1997 |
| WO | WO 99/67427 | 12/1999 |

OTHER PUBLICATIONS

Whitcomb et al. Hypersusceptibility to non-nucleoside reverse transcriptase inhibitors in HIV-1: clinical, phenotypic and genotypic correlates. AIDS 2002, vol. 16, Issue 15, pp. F41-F47.*
Haubrich et al. The clinical relevance of non-nucleoside reverse transcriptase inhibitor hypersusceptibility. AIDS 2002, vol. 16, Issue 15, pp. F33-F40.*
Shulman et al. Phenotypic hypersusceptibility to non-nucleoside reverse transcriptase inhibitors in treatmen-experienced HIV-infected patients: impact on virological response to efavirenz-based therapy. AIDS 2001, vol. 15, p. 1125-1132.*
Matamoros et al., The Journal of Biological Chemistry, Jun. 4, 2004, 279(23):24569-24577.*
Shafer et al., AIDS Rev., 2000, 2(4): 211-228.*
Abravaya, K. et al., Detection of point mutations with a modified ligase chain reaction (Gap-LCR), 1995, Nucl. Acids Res., 23:675-682.
Altschul, S. et al., Basic Local Alignment Search Tool, 1990, J. Mol. Biol., 215:403-10.
Altschul, S. et al., Gapped BLAST and PSI-BLAST: a new generation of protein database search programs, 1997, Nucleic Acids Res., 25:3389-3402.
Barany, F., Genetic disease detection and DNA amplification using cloned thermostable ligase, 1991, Proc. Natl. Acad. Sci. U.S.A., 88:189-193.

(Continued)

*Primary Examiner* — Nicole Kinsey White
(74) *Attorney, Agent, or Firm* — Kilpatrick Townsend & Stockton LLP

(57) ABSTRACT

This invention relates to methods for determining hypersusceptibility of HIV-1 viruses to non-nucleoside reverse transcriptase inhibitors (NNRTIs) based on the viral genotypes. The methods generally comprise detecting, in a gene encoding reverse transcriptase of the HIV-1, the presence of a mutation at codon 65, 69, or 74 alone or in combination with one or more mutations at certain other codons. Combinations of mutations associated with hypersusceptibility to NNRTIs are also disclosed.

12 Claims, 6 Drawing Sheets

Figure 1:
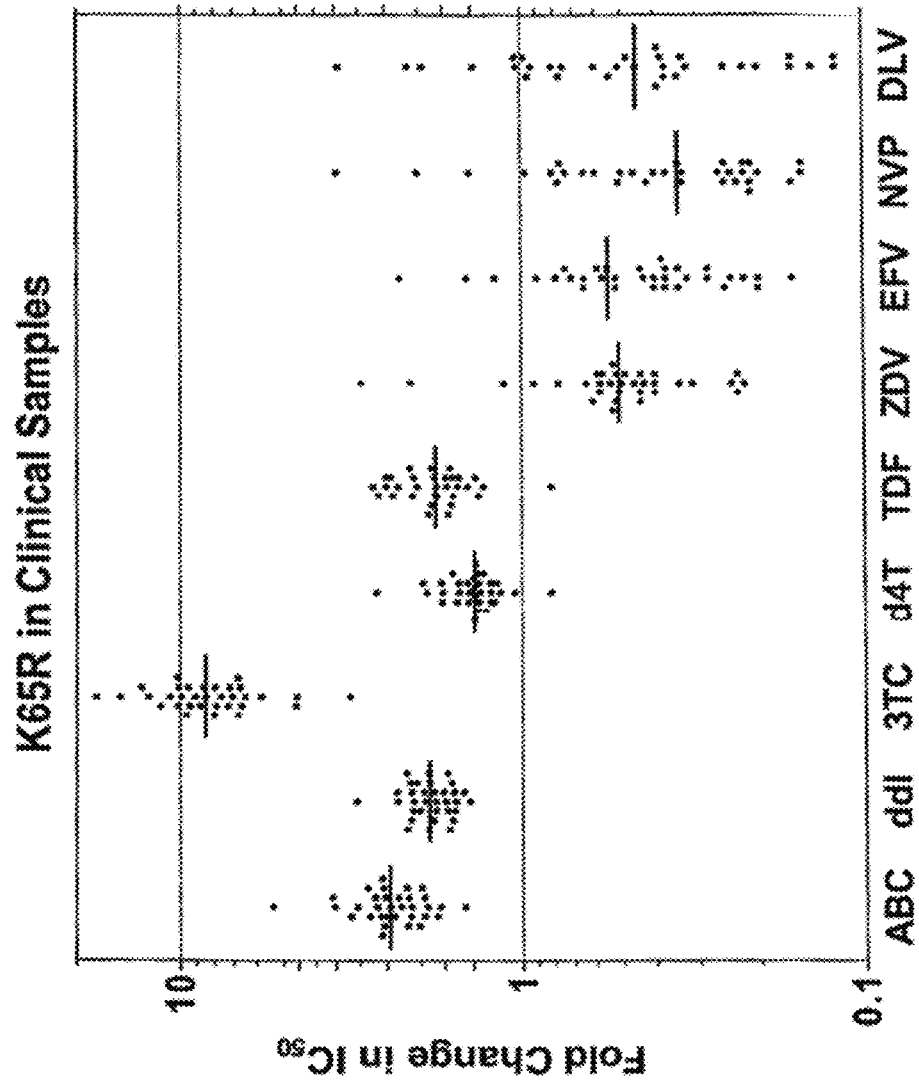

Specification includes a Sequence Listing.

(56) References Cited

OTHER PUBLICATIONS

Barnes, W., PCR amplification of up to 35-kb DNA with high fidelity and high yield from λ bacteriophage templates, 1994, Proc. Natl. Acad. Sci. USA, 91:2216-2220.

Bosch, R. et al., Evaluation of cutpoints for phenotypic hypersusceptibility to efavirenz, 2003, AIDS, 17:2395-2396.

Cotton, R. et al., Reactivity of cytosine and thymine in single-base-pair mismatches with hydroxylamine and osmium tetroxide and its application to the study of mutations, 1988, Proc. Natl. Acad. Sci. U.S.A., 85:4397-4401.

Current Protocols in Molecular Biology, Ausubel, F.M. et al., eds., John Wiley & Sons, NY, 2010 Table of Contents and list of yearly supplements.

Durant, J. et al., Drug-resistance genotyping in HIV-1 therapy: the VIRAD APT randomised controlled trial, 1999, Lancet, 353:2195-9.

Eisenberg, D. et al., Analysis of Membrane and Surface Protein Sequences with the Hydrophobic Moment Plot, 1984, J. Mol. Biol., 179: 125-142.

Faham, M. and Cox, D., A Novel In Vivo Method to Detect DNA Sequence Variation, 1995, Genome Res., 5:474-482.

Fischer, S. et al., DNA fragments differing by single base-pair substitutions are separated in denaturing gradient gels: Correspondence with melting theory, 1983, Proc. Natl. Acad. Sci. U.S.A., 80:1579-83.

Freedman, D. et al., 1980, Statistics, W. W. Norton, New York.

Gervaix, A. et al., A new reporter cell line to monitor HIV infection and drug susceptibiiity in vitro, 1997, Proc. Natl. Acad. Sci. U.S.A., 94:4653-4658.

Hammer, S. et al., Dual vs. Single Protease Inhibitor Therapy Following Antiretroviral Treatment Failure: A Randomized Trial, 2002, J.A.M.A,. 288:169-80.

Haubrich, R. et al., The clinical relevance of non-nucleoside reverse transcriptase inhibitor hypersusceptibility: a prospective cohort analysis, 2002, AIDS, 16:33-40.

Hertogs, K. et al., A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs, 1998, Antimicrob. Agents Chemother., 42(2):269-76.

Kan, Y. and Dozy, A., Antenatal Diagnosis of Sickle-Cell Anemia by D.N.A. Analysis of Amniotic-Fluid Cells, 1987, Lancet ii:910-912.

Landergren, U. et al., A Ligase-Mediated Gene Detection Technique 1988, Science, 241:1077-1080.

Lu, J. et al., A Novel Recombinant Marker Virus Assay for Comparing the Relative Fitness of HIV-1 Reverse Transcriptase Variants, 2001, JAIDS, 27:7-13.

Lucas, S., The pathology of HIV infection, 2002, Lepr. Rev., 73(1):64-71.

Maxam, A. et al., Sequencing end-labeled DNA with base-specific chemical cleavages, 1980, Methods in Enzymology, 65:499-560.

Mellors, J. et al., "Mutations in HIV-1 Reverse Transcriptase and Protease Associated with Drug Resistance," 1995, Mutations in RT and Protease, III:93-105.

Messing, J. et al., A system for shotgun DNA sequencing, 1981, Nucl. Acids Res., 9:309-321.

Myers, R. et al., Detection of Single Base Substitutions by Ribonuclease Cleavage at Mismatches in RNA:DNA Duplexes, 1985, Science, 230:1242-1246.

Nikiforov, T. et al., Genetic Bit Analysis: a solid phase method for typing single nucleotide polymorphisms, 1994, Nucl. Acids Res., 22:4167-4175.

Norris, T., HIV Update, 2002, Radiol. Technol., 73(4):339-363.

Orita, M. et al., Rapid and Sensitive Detection of Point Mutations and DNA Polymorphisms, 1989, Genomics, 5:874-879.

Orita, M et al., Detection of polymorphisms of human DNA by gel electrophoresis as single-strand conformation polymorphisms, 1989, Proc. Natl. Acad. Sci. USA, 86:2766-2770.

Orum, H. et al., Single base pair mutation analysis by PNA directed PCR Clamping, 1993, Nucl. Acids Res., 21:5332-5356.

PCR Strategies, 1995, Innis et al.(eds.), Academic Press, Inc.

Petropoulos, C. et al., A Novel Phenotypic Drug Susceptibility Assay for Human Immunodeficiency Virus Type 1, 2000, Antimicrob. Agents Chemother., 44:920-928.

Race, E. et al., Analysis of HIV Cross-Resistance to Protease Inhibitors using a Rapid Single-Cycle Recombinant Virus Assay for Patients Failing on Combination Therapies, 1999, AIDS, 13:2061-2068.

Russell, W. et al., Specific-locus test shows ethylnitrosourea to be the most potent mutagen in the mouse., 1979, Proc. Nat. Acad. Sci. USA, 76:5818-5819.

Russell, W., Factors Affecting Mutagenicity of Ethylnitrosourea in the Mouse Specific-Locus Test and Their Bearing on Risk Estimation, In Environmental Mutagens and Carcinogens: Proceedings of the Third International Conference on Environmental Mutagens, Tokyo, Mishima and Kyoto, 1982.

Sambrook, J. et al., 2001, Molecular Cloning: A Laboratory Manual, Cold Spring Harbor Laboratory, 3rd ed., NY.

Sanger, F. et al., DNA sequencing with chain-terminating inhibitors, 1977, Proc. Natl. Acad. Sci. USA, 74:5463-5467.

Shi, C. et al., A Recombinant Retroviral System for Rapid In Vivo Analysis of Human Immunodeficiency Virus Type 1 Susceptibility to Reverse Transcriptase Inhibitors, 1997, Antimicrob. Agents Chemother., 41(12):2781-85.

Shulman, N. et al., Phenotypic hypersusceptibility to non-nucleoside reverse transcriptase inhibitors in treatment-experienced HIV-infected patients: impact on virological response to efavirenz-based therapy, 2001, AIDS, 15:1125-1132.

Sarker, G. and Sommer, S.S., The "Megaprimer" Method of Site-Directed Mutagenesis, 1990, Biotechniques, 8:404-407.

Southern, E., Detection of Specific Sequences Among DNA Fragments Separated by Gel Electrophoresis, 1975, J. Mol. Biol., 98:503-517.

Syvanen, A. et al., A Primer-Guided Nucleotide Incorporation Assay in the Genotyping of Apolipoprotein E, 1990, Genomics, 8:684-692.

Thiede, C. et al., Simple and sensitive detection of mutations in the ras proto-oncogenes using PNA-mediated PCR clamping, 1996, Nucl. Acids Res., 24:983-984.

Wagner, R. et al., Mutation detection using immobilized mismatch binding protein (MutS), 1995, Nucl. Acids Res., 23:3944-3948.

Youil, R. et al., Screening for mutations by enzyme mismatch cleavage with T4 endonuclease VII, 1995, Proc. Natl. Acad. Sci. U.S.A., 92:87-91.

Colonno, R. et al., Identification of I50L as the Signature Atazanavir (ATV)—Resistance Mutation in Treatment-Naïve HIV-1—Infected Patients Receiving ATV-Containing Regimens, 2004, JID, 189:1802-1810.

Kroodsma, K. et al., Detection of Drug Resistance Mutations in the Human Immunodeficiency Virus pe 1 (HIV-I) pot Gene: Differences in Semen and Blood HIV-1 RNA and Proviral DNA, 1994, Journal of Infectious Diseases, 170: 1292-11295.

Hirsch, S. et al., Antiretroviral Drug Resistance Testing in Adult HIV-1 Infection: 2008 Recommendations of an International AIDS Society—USA Panel, 2008, Clinical Infectious Diseases, 47:266-85.

Gupta, S. et al., Combinations of Mutations in the Connection Domain of Human Immunodeficiency Virus Type 1 Reverse Transcriptase: Assessing the Impact on Nucleoside and Non-nucleoside Reverse Transcriptase Inhibitor Resistance, 2010, Antimicrob. Agents Chemother., 54:1973-1980.

Whitcomb, J. et al., Broad Nucleoside Reverse-Transcriptase Inhibitor Cross-Resistance in Human Immunodeficiency Virus Type 1 Clinical Isolates, 2003, Journal of Infectious Diseases, 188:992-1000.

Mellors, J. et al., "Mutations in HIV-1 Reverse Transcriptase and Protease Associated with Drug Resistance," 1995, Mutations in RT and Protease, 111:93-105.

GenBank Accession No. AF324493, HIV-1 vector pNL4-3, complete sequence, 1986.

\* cited by examiner

METHODS FOR DETERMINING HYPERSUSCEPTIBILITY OF HIV-1 TO NON-NUCLEOSIDE REVERSE TRANSCRIPTASE INHIBITORS

PRIOR RELATED APPLICATIONS

This application is a continuation application of U.S. application Ser. No. 11/884,667 filed Aug. 17, 2007 (now U.S. Pat. No. 8,178,291), which is a § 371 national phase application of PCT Application No. PCT/US06/05511 filed Feb. 16, 2006 (expired), which claims priority to U.S. provisional application No. 60/654,738 filed Feb. 18, 2005 and U.S. Provisional Application No. 60/685,301 filed May 26, 2005. Each of these applications is hereby incorporated by reference in its entirety.

1. FIELD OF INVENTION

This invention relates, in part, to methods and compositions for determining hypersusceptibility of a human immunodeficiency virus ("HIV") to the non-nucleoside reverse transcriptase inhibitors ("NNRTIs") efavirenz ("EFV"), nevirapine ("NVP"), and delavirdine ("DLV") by detecting the presence of a mutation or combinations of mutations in the gene encoding HIV reverse transcriptase that are associated with hypersusceptibility to the NNRTIs.

2. BACKGROUND OF THE INVENTION

More than 60 million people have been infected with the human immunodeficiency virus ("HIV"), the causative agent of acquired immune deficiency syndrome ("AIDS"), since the early 1980s. See Lucas, 2002, *Lepr Rev.* 73(1):64-71. HIV/AIDS is now the leading cause of death in sub-Saharan Africa, and is the fourth biggest killer worldwide. At the end of 2001, an estimated 40 million people were living with HIV globally. See Norris, 2002, *Radiol Technol.* 73 (4):339-363.

Modern anti-HIV drugs target different stages of the HIV life cycle and a variety of enzymes essential for HIV's replication and/or survival. Amongst the drugs that have so far been approved for AIDS therapy are nucleoside reverse transcriptase inhibitors ("NRTIs") such as AZT, ddI, ddC, d4T, 3TC, and abacavir; nucleotide reverse transcriptase inhibitors such as tenofovir; non-nucleoside reverse transcriptase inhibitors ("NNRTIs") such as nevirapine, efavirenz, and delavirdine; protease inhibitors ("PIs") such as saquinavir, ritonavir, indinavir, nelfinavir, amprenavir, lopinavir and atazanavir; and fusion inhibitors, such as enfuvirtide.

Nonetheless, in the vast majority of subjects none of these antiviral drugs, either alone or in combination, proves effective either to prevent eventual progression of chronic HIV infection to AIDS or to treat acute AIDS. This phenomenon is due, in part, to the high mutation rate of HIV and the rapid emergence of mutant HIV strains that are resistant to antiviral therapeutics upon administration of such drugs to infected individuals.

Many such mutant strains have been characterized in order to correlate presence of the mutations in the strains with resistant or susceptible phenotypes. For example, the M184V mutation in reverse transcriptase is known to correlate with resistance to a number of NRTIs, including, for example, abacavir and lamivudine. See, e.g., Durant et al., 1998, *Lancet* 353:2195-9. In addition, the M184V mutation is also known to correlate with hypersusceptibility to efavirenz. See Shulman et al., 2001, *AIDS* 15:1125-1132. Thus, a given mutation may correlate with resistance to one or more antiviral agent and hypersusceptibility to one or more others.

Further, hypersusceptibility to NNRTIs such as efavirenz and/or nevirapine has been shown to be clinically relevant to treatment of patients infected with HIV-1 hypersusceptible to treatment with such agents. See, for example, Haubrich et al., 2002, *AIDS* 16:33-40; Shulman et al., 2001, *AIDS* 15:1125-1132; Bosch et al., 2003, *AIDS* 17:2395-2396; and Hammer et al., 2002, *J.A.M.A.* 288:169-80.

Though numerous mutations associated with both resistance and susceptibility to particular anti-viral agents have been identified, the effects of these mutations on resistance or susceptibility to other antiviral agents in many cases remains obscure. Thus, an analysis that identifies the effects of mutations associated with resistance to one antiviral agent on resistance or susceptibility to other antiviral agents would be very useful in guiding selection of particular antiviral agents in guiding therapeutic decisions in the treatment of HIV-infected individuals. Further, in view of the clinical relevance of NNRTI hypersusceptibility, a more complete understanding of mutations associated with such hypersusceptibility is also needed. For the first time, these, as well as other unmet needs, will be achievable as a result of the invention described hereinafter.

3. SUMMARY OF THE INVENTION

The present invention provides methods for determining that an HIV-1 is hypersusceptible to a NNRTI. In the methods, hypersusceptibility to a NNRTI can be determined by detecting the presence of mutations that correlate with hypersusceptibility to a NNRTI.

Thus, in certain aspects, the invention provides a method for determining that an HIV-1 is hypersusceptible to a NNRTI, comprising detecting in a gene encoding reverse transcriptase of the HIV-1 the presence of a mutation at codon 65 or 69, wherein the presence of the mutation correlates with hypersusceptibility to a NNRTI, thereby determining that the HIV-1 is hypersusceptible to the NNRTI. In certain embodiments, the methods comprise detecting the presence of a mutation at codon 65 or 69 in combination with a mutation at codon 184, wherein the presence of the mutations correlates with hypersusceptibility to a NNRTI, thereby determining that the HIV-1 is hypersusceptible to the NNRTI. The presence of the mutations associated with hypersusceptibility to a NNRTI can be detected according to any method known to one of skill in the art without limitation. Methods for detecting such mutations are described extensively below.

In other aspects, the invention provides a method for determining that an HIV-1 is hypersusceptible to a NNRTI, comprising detecting in a gene encoding reverse transcriptase of the HIV-1 the presence of a mutation at codon 70 in combination with mutations in at least two of codons 41, 67, 210, 215, and 219, wherein the presence of the mutations correlates with hypersusceptibility to a NNRTI, thereby determining that the HIV-1 is hypersusceptible to the NNRTI. The presence of the mutations associated with hypersusceptibility to a NNRTI can be detected according to any method known to one of skill in the art without limitation. Methods for detecting such mutations are described extensively below.

In still other aspects, the invention provides a method for determining that an HIV-1 is hypersusceptible to a NNRTI, comprising detecting in a gene encoding reverse transcriptase of the HIV-1 the presence of a mutation at codon 215 in combination with mutations in at least two of codons 41, 67, 70, 210, and 219, wherein the presence of the mutations correlates with hypersusceptibility to a NNRTI, thereby determining that the HIV-1 is hypersusceptible to the NNRTI. In certain embodiments, the methods comprise detecting in a gene encoding reverse transcriptase of the HIV-1 the presence of a mutation at codon 215 in combination with mutations in at least two of codons 41, 67, 70, 210, and 219 and with a mutation at codon 118, wherein the presence of the mutations correlates with hypersusceptibility to a NNRTI, thereby determining that the HIV-1 is hypersusceptible to the NNRTI. The presence of the mutations associated with hypersusceptibility to a NNRTI can be detected according to any method known to one of skill in the art without limitation. Methods for detecting such mutations are described extensively below.

In yet other aspects, the invention provides a method for determining that an HIV-1 is hypersusceptible to a NNRTI, comprising detecting in a gene encoding reverse transcriptase of the HIV-1 the presence of a mutation at codon 74, wherein the presence of the mutation correlates with hypersusceptibility to a NNRTI, thereby determining that the HIV-1 is hypersusceptible to the NNRTI. The presence of the mutations associated with hypersusceptibility to a NNRTI can be detected according to any method known to one of skill in the art without limitation. Methods for detecting such mutations are described extensively below.

4. BRIEF DESCRIPTION OF THE FIGURES

FIG. 1 presents the distribution of fold change in $IC_{50}$ observed in the presence of various antiviral agents for HIV-1 isolated from 36 clinical samples comprising the K65R mutation in reverse transcriptase.

Figure 2:
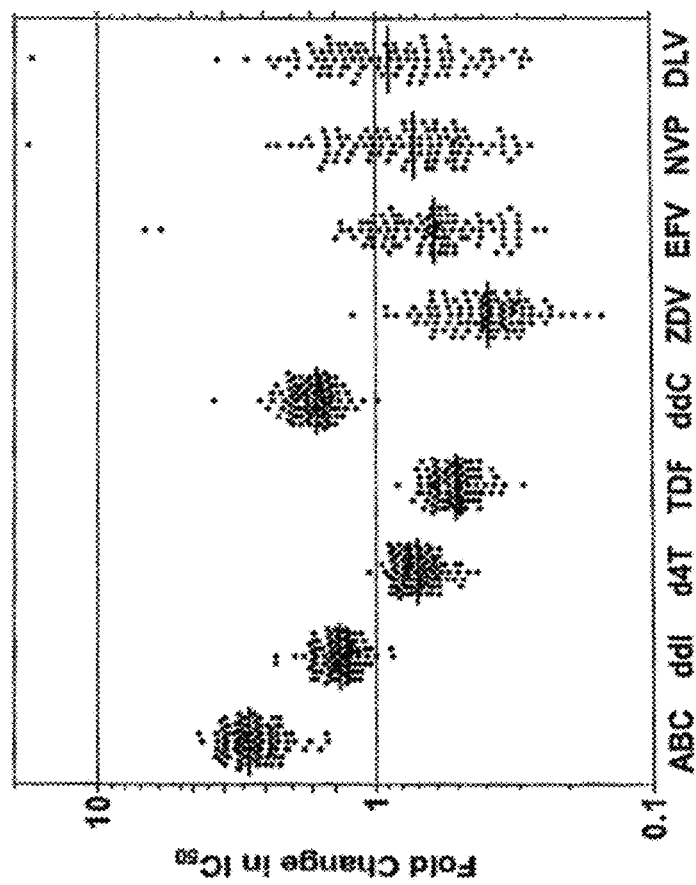

FIG. 2 presents the distribution of fold change in $IC_{50}$ observed in the presence of various antiviral agents for HIV-1 isolated from 100 randomly selected clinical samples comprising the M184V mutation in reverse transcriptase.

Figure 3:
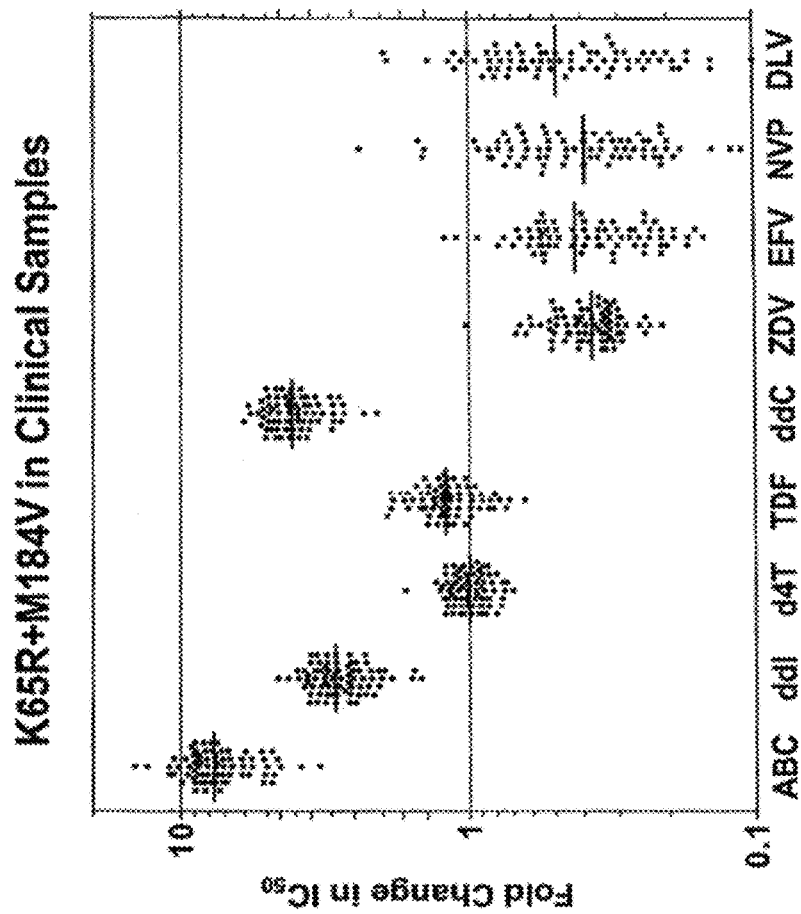

FIG. 3 presents the distribution of fold change in $IC_{50}$ observed in the presence of various antiviral agents for HIV-1 isolated from 75 clinical samples comprising both the K65R and M184V mutations in reverse transcriptase.

Figure 4:
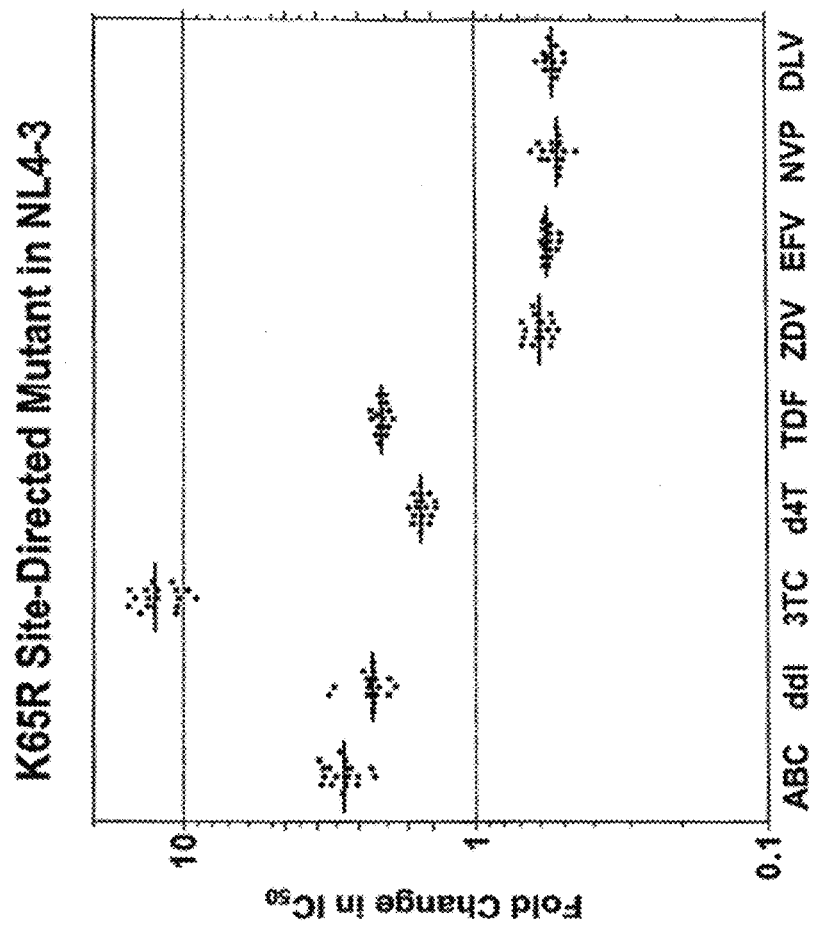

FIG. 4 presents the distribution of fold change in $IC_{50}$ observed in the presence of various antiviral agents for multiple measurements of an HIV-1 site-directed mutant that comprises the K65R mutation in reverse transcriptase.

Figure 5:
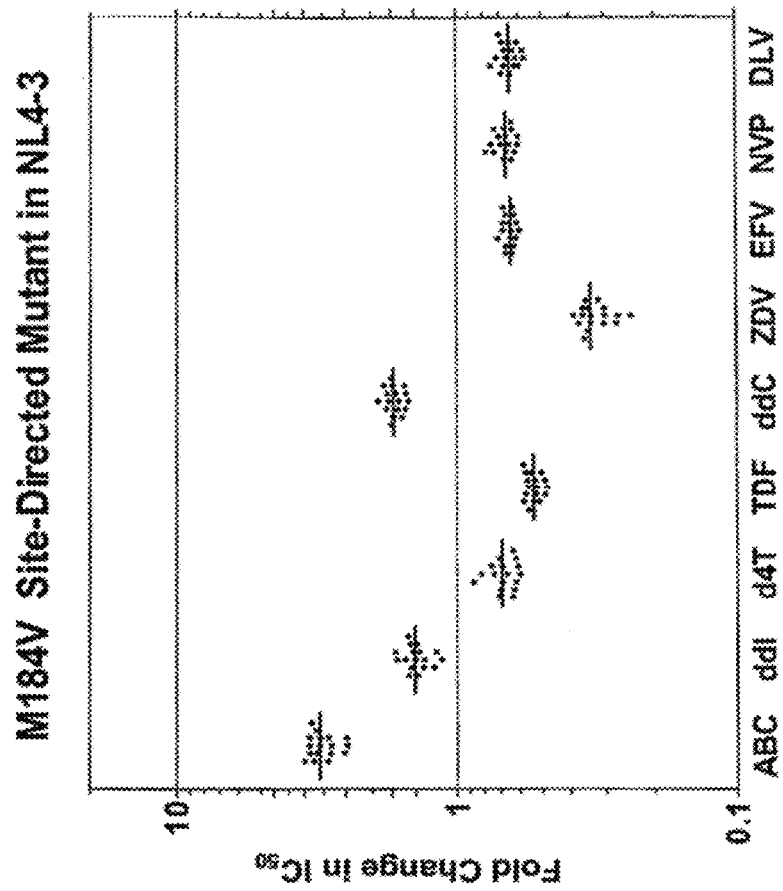

FIG. 5 presents the distribution of fold change in $IC_{50}$ observed in the presence of various antiviral agents for multiple measurements of an HIV-1 site-directed mutant that comprises the M184V mutation in reverse transcriptase.

Figure 6:
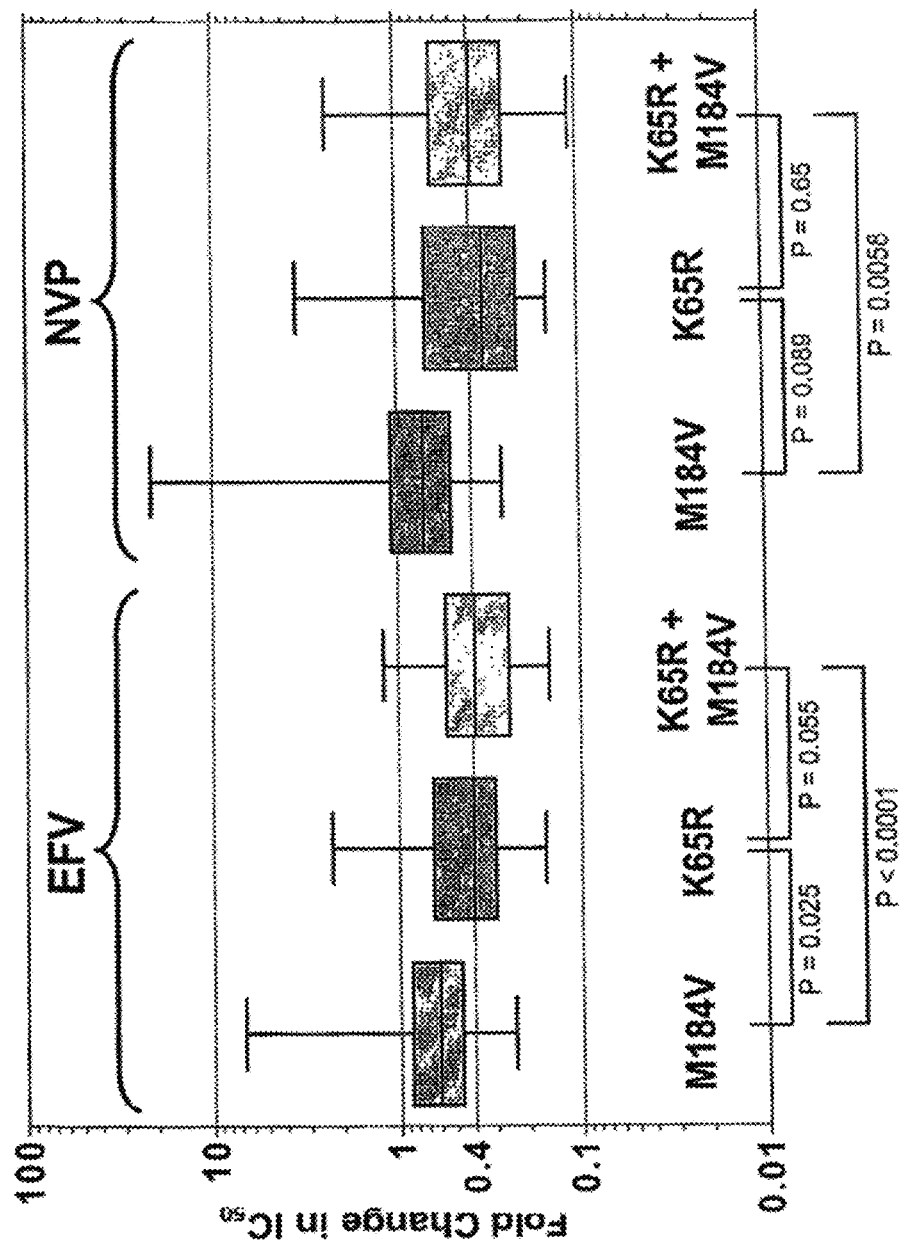

FIG. 6 presents box plots showing EFV and NVP $IC_{50}$ fold change distributions observed for HIV-1 clinical isolates comprising K65R, M184V, and both K65R and M184V.

5. DETAILED DESCRIPTION OF THE INVENTION

The present invention provides methods for determining that an HIV-1 is hypersusceptible to antiviral therapy with a NNRTI. The methods generally comprise detecting the presence of mutations in the HIV-1 gene encoding RT that significantly correlate with hypersusceptibility to a NNRTI.

5.1. Abbreviations

"NRTI" is an abbreviation for nucleoside reverse transcriptase inhibitor.

"NNRTI" is an abbreviation for non nucleoside reverse transcriptase inhibitor.

"PI" is an abbreviation for protease inhibitor.

"PR" is an abbreviation for protease.

"RT" is an abbreviation for reverse transcriptase.

"PCR" is an abbreviation for "polymerase chain reaction."

"HBV" is an abbreviation for hepatitis B virus.

"HCV" is an abbreviation for hepatitis C virus.

"HIV" is an abbreviation for human immunodeficiency virus.

"EFV" is an abbreviation for the NNRTI efavirenz.

"DLV" is an abbreviation for the NNRTI delavirdine.

"NVP" is an abbreviation for the NNRTI nevirapine.

The amino acid notations used herein for the twenty genetically encoded L-amino acids are conventional and are as follows:

| Amino Acid | One-Letter Abbreviation | Three Letter Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Unless noted otherwise, when polypeptide sequences are presented as a series of one-letter and/or three-letter abbreviations, the sequences are presented in the N→C direction, in accordance with common practice.

Individual amino acids in a sequence are represented herein as AN, wherein A is the standard one letter symbol for the amino acid in the sequence, and N is the position in the sequence. Mutations are represented herein as $A_1NA_2$, wherein $A_1$ is the standard one letter symbol for the amino acid in the reference protein sequence, $A_2$ is the standard one letter symbol for the amino acid in the mutated protein sequence, and N is the position in the amino acid sequence. For example, a G25M mutation represents a change from glycine to methionine at amino acid position 25. Mutations may also be represented herein as $NA_2$, wherein N is the position in the amino acid sequence and $A_2$ is the standard one letter symbol for the amino acid in the mutated protein sequence (e.g., 25M, for a change from the wild-type amino acid to methionine at amino acid position 25). Additionally, mutations may also be represented herein as $A_1NX$, wherein $A_1$ is the standard one letter symbol for the amino acid in the reference protein sequence, N is the position in the amino acid sequence, and X indicates that the mutated amino acid can be any amino acid (e.g., G25X represents a change from glycine to any amino acid at amino acid position 25). This notation is typically used when the amino acid in the mutated protein sequence is either not known or, if the amino acid in the mutated protein sequence could be any amino acid, except that found in the reference protein sequence. The amino acid positions are numbered based on the fall-length sequence of the protein from which the region encompassing the mutation is derived. Representations of nucleotides and point mutations in DNA sequences are analogous.

The abbreviations used throughout the specification to refer to nucleic acids comprising specific nucleobase sequences are the conventional one-letter abbreviations. Thus, when included in a nucleic acid, the naturally occurring encoding nucleobases are abbreviated as follows: adenine (A), guanine (G), cytosine (C), thymine (T) and uracil (O). Unless specified otherwise, single-stranded nucleic acid sequences that are represented as a series of one-letter abbreviations, and the top strand of double-stranded sequences, are presented in the 5'→3' direction.

5.2. Definitions

As used herein, the following terms shall have the following meanings:

A "phenotypic assay" is a test that measures a phenotype of a particular virus, such as, for example, HIV, or a population of viruses, such as, for example, the population of HIV infecting a subject. The phenotypes that can be measured include, but are not limited to, the resistance or susceptibility of a virus, or of a population of viruses, to a specific anti-viral agent or that measures the replication capacity of a virus.

A "genotypic assay" is an assay that determines a genotype of an organism, a part of an organism, a population of organisms, a gene, a part of a gene, or a population of genes. Typically, a genotypic assay involves determination of the nucleic acid sequence of the relevant gene or genes. Such assays are frequently performed in HIV to establish, for example, whether certain mutations are associated with drug resistance or hypersusceptibility or altered replication capacity are present.

As used herein, "genotypic data" are data about the genotype of, for example, a virus. Examples of genotypic data include, but are not limited to, the nucleotide or amino acid sequence of a virus, a population of viruses, a part of a virus, a viral gene, a part of a viral gene, or the identity of one or more nucleotides or amino acid residues in a viral nucleic acid or protein.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. Exemplary levels of sequence identity include, but are not limited to, 60, 70, 80, 85, 90, 95, 98% or more sequence identity to a given sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. Exemplary levels of sequence homology include, but are not limited to, 60, 70, 80, 85, 90, 95, 98% or more sequence homology to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, *J. Mol. Biol.* 215:403-10 (with special reference to the published default setting, i.e., parameters w=4, t=17) and Altschul et al., 1997, *Nucleic Acids Res.,* 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

A preferred alignment of selected sequences in order to determine "% identity" between two or more sequences, is performed using for example, the CLUSTAL-X program, operated with default parameters, including an open gap penalty of 10.0, an extended gap penalty of 0.1, and a BLOSUM 30 similarity matrix.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Ala (A), Gly (G), Ile (I), Leu (L), Met (M) and Val (V).

"Hydrophilic Amino Acid" refers to an amino acid exhibiting a hydrophobicity of less than zero according to the normalized consensus hydrophobicity scale of Eisenberg et al., 1984, *J. Mol. Biol.* 179:125-142. Genetically encoded hydrophilic amino acids include Arg (R), Asn (N), Asp (D), Glu (E), Gln (Q), His (H), Lys (K), Ser (S) and Thr (T).

"Hydrophobic Amino Acid" refers to an amino acid exhibiting a hydrophobicity of greater than zero according to the normalized consensus hydrophobicity scale of Eisenberg et al., 1984, *J. Mol. Biol.* 179:125-142. Genetically encoded hydrophobic amino acids include Ala (A), Gly (G), Ile (I), Leu (L), Met (M), Phe (F), Pro (P), Trp (W), Tyr (Y) and Val (V).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

"Basic Amino Acid" refers to a hydrophilic amino acid having a side chain pK value of greater than 7. Basic amino acids typically have positively charged side chains at physiological pH due to association with a hydrogen ion. Genetically encoded basic amino acids include Arg (R), His (H) and Lys (K).

A "mutation" is a change in an amino acid sequence or in a corresponding nucleic acid sequence relative to a reference nucleic acid or polypeptide. For embodiments of the invention comprising HIV protease or reverse transcriptase, the reference nucleic acid encoding protease or reverse transcriptase is the protease or reverse transcriptase coding sequence, respectively, present in NL4-3 HIV (GenBank Accession No. AF324493). Likewise, the reference protease or reverse transcriptase polypeptide is that encoded by the NL4-3 HIV sequence. Although the amino acid sequence of a peptide can be determined directly by, for example, Edman degradation or mass spectroscopy, more typically, the amino sequence of a peptide is inferred from the nucleotide sequence of a nucleic acid that encodes the peptide. Any method for determining the sequence of a nucleic acid known in the art can be used, for example, Maxam-Gilbert sequencing (Maxam et al., 1980, *Methods in Enzymology* 65:499), dideoxy sequencing (Sanger et al., 1977, *Proc. Natl. Acad. Sci. USA* 74:5463) or hybridization-based approaches (see e.g., Sambrook et al., 2001, *Molecular Cloning: A Laboratory Manual*, Cold Spring Harbor Laboratory, 3$^{rd}$ ed., NY; and Ausubel et al., 1989, *Current Protocols in Molecular Biology*, Greene Publishing Associates and Wiley Interscience, NY).

A "mutant" is a virus, gene or protein having a sequence that has one or more changes relative to a reference virus, gene or protein.

The terms "peptide," "polypeptide" and "protein" are used interchangeably throughout.

The term "wild-type" refers to a viral genotype that does not comprise a mutation known to be associated with drug resistance.

The terms "polynucleotide," "oligonucleotide" and "nucleic acid" are used interchangeably throughout.

5.3. Methods of Determining Hypersusceptibility to a NNRTI

In certain aspects, the present invention provides methods for determining that an HIV-1 is resistant or susceptible to a NNRTI. In general, the methods comprise detecting the presence of mutations significantly correlated with NNRTI hypersusceptibility in the gene encoding reverse transcriptase of the HIV-1, as demonstrated by the examples below.

Therefore, in certain embodiments, the invention provides a method for determining that an human immunodeficiency virus 1 (HIV-1) is hypersusceptible to a NNRTI, comprising detecting in a gene encoding reverse transcriptase of the HIV-1 the presence of a mutation at codon 65 or 69, wherein the presence of the mutation correlates with hypersusceptibility to a NNRTI, thereby determining that the HIV-1 is hypersusceptible to the NNRTI. In certain embodiments, a mutation at codon 65 is detected. In certain embodiments, the mutation at codon 65 encodes arginine (R). In certain embodiments, a mutation at codon 69 is detected. In certain embodiments, the mutation at codon 69 encodes alanine (A), aspartic acid (D), asparagine (N), or serine (S). In certain embodiments, the NNRTI is EFV, DLV, or NVP. In certain embodiments, the NNRTI is EFV. In certain embodiments, the NNRTI is DLV. In certain embodiments, the NNRTI is NVP.

In certain embodiments, the method further comprises detecting in the gene encoding reverse transcriptase the presence of a mutation at codon 184, wherein the presence of the mutations at codon 184 and at codon 65 or 69 correlates with hypersusceptibility to a NNRTI, thereby determining that the HIV-1 is hypersusceptible to the NNRTI. In certain embodiments, the mutation at codon 184 encodes valine (V) or isoleucine (I). In certain embodiments, a mutation at codon 65 is detected. In certain embodiments, the mutation at codon 65 encodes arginine (R). In certain embodiments, a mutation at codon 69 is detected. In certain embodiments, the mutation at codon 69 encodes alanine (A), aspartic acid (D), asparagine (N), or serine (S). In certain embodiments, the NNRTI is EFV, DLV, or NVP. In certain embodiments, the NNRTI is EFV. In certain embodiments, the NNRTI is DLV. In certain embodiments, the NNRTI is NVP.

In another aspect, the invention provides a method for determining that an HIV-1 is hypersusceptible to a NNRTI, comprising detecting in a gene encoding reverse transcriptase of the HIV-1 the presence of a mutation at codon 70 in combination with mutations in at least two of codons 41, 67, 210, 215, and 219, wherein the presence of the mutations correlates with hypersusceptibility to a NNRTI, thereby determining that the HIV-1 is hypersusceptible to the NNRTI. In certain embodiments, the mutation at codon 70 encodes arginine (R). In certain embodiments, the mutation at codon 41 encodes leucine (L). In certain embodiments, the mutation at codon 67 encodes asparagine (N). In certain embodiments, the mutation at codon 210 encodes tryptophan (W). In certain embodiments, the mutation at codon 215 encodes tyrosine (Y) or F. In certain embodiments, the mutation at codon 219 encodes glutamic acid (E), histidine H, asparagine (N), glutamine (Q), or arginine (R). In certain embodiments, the methods comprise detecting a mutation in at least one of codons 41, 67, 210, 215, and 219. In certain embodiments, the methods comprise detecting a mutation in at least three of codons 41, 67, 210, 215, and 219. In certain embodiments, the methods comprise detecting a mutation in at least four of codons 41, 67, 210, 215, and 219. In certain embodiments, the methods comprise detecting a mutation in each of codons 41, 67, 210, 215, and 219. In certain embodiments, the NNRTI is EFV, DLV, or NVP. In certain embodiments, the NNRTI is EFV. In certain embodiments, the NNRTI is DLV. In certain embodiments, the NNRTI is NVP.

In another aspect, the invention provides a method for determining that an HIV-1 is hypersusceptible to a NNRTI, comprising detecting in a gene encoding reverse transcriptase of the HIV-1 the presence of a mutation at codon 215 in combination with mutations in at least two of codons 41, 67, 70, 210, and 219, wherein the presence of such mutations correlates with hypersusceptibility to a NNRTI, thereby determining that the HIV-1 is hypersusceptible to the NNRTI. In certain embodiments, the mutation at codon 215 encodes tyrosine (Y). In certain embodiments, the mutation at codon 41 encodes leucine (L). In certain embodiments, the mutation at codon 67 encodes asparagine (N). In certain embodiments, the mutation at codon 70 encodes arginine (R). In certain embodiments, the mutation at codon 210 encodes tryptophan (W). In certain embodiments, the mutation at codon 219 encodes glutamic acid (E), histidine H, asparagine (N), glutamine (Q), or arginine (R). In certain embodiments, the NNRTI is EFV, DLV, or NVP. In certain embodiments, the NNRTI is EFV. In certain embodiments, the NNRTI is DLV. In certain embodiments, the NNRTI is NVP.

In certain embodiments, the method further comprise detecting in the gene encoding reverse transcriptase the presence of a mutation at codon 118, wherein the presence of the mutation at codon 215 in combination with mutations in at least two of codons 41, 67, 70, 210, and 219 and in combination with a mutation at codon 118 correlates with hypersusceptibility to a NNRTI, thereby determining that the HIV-1 is hypersusceptible to the NNRTI. In certain embodiments, the mutation at codon 215 encodes tyrosine (Y). In certain embodiments, the mutation at codon 41 encodes leucine (L). In certain embodiments, the mutation at codon 67 encodes asparagine (N). In certain embodiments, the mutation at codon 70 encodes arginine (R). In certain embodiments, the mutation at codon 210 encodes tryptophan (W). In certain embodiments, the mutation at codon 118 encodes isoleucine (I). In certain embodiments, the mutation at codon 219 encodes glutamic acid (E), histidine H, asparagine (N), glutamine (Q), or arginine (R). In certain embodiments, the methods comprise detecting a mutation in at least one of codons 41, 67, 70, 210, and 219. In certain embodiments, the methods comprise detecting a mutation in at least three of codons 41, 67, 70, 210, and 219. In certain embodiments, the methods comprise detecting a mutation in at least four of codons 41, 67, 70, 210, and 219. In certain embodiments, the methods comprise detecting a mutation in each of codons 41, 67, 70, 210, and 219. In certain embodiments, the NNRTI is EFV, DLV, or NVP. In certain embodiments, the NNRTI is EFV. In certain embodiments, the NNRTI is DLV. In certain embodiments, the NNRTI is NVP.

In another aspect, the invention provides a method for determining that an HIV-1 is hypersusceptible to a NNRTI, comprising detecting in a gene encoding reverse transcriptase of the HIV-1 the presence of a mutation at codon 74, wherein the presence of such mutations correlates with hypersusceptibility to a NNRTI, thereby determining that the HIV-1 is hypersusceptible to the NNRTI. In certain embodiments, the mutation at codon 74 encodes valine (V). In certain embodiments, the NNRTI is EFV, DLV, or NVP. In certain embodiments, the NNRTI is EFV. In certain embodiments, the NNRTI is DLV. In certain embodiments, the NNRTI is NVP.

In another aspect, the invention provides a method for determining that an HIV-1 is hypersusceptible to a NNRTI, comprising detecting in a gene encoding reverse transcriptase of the HIV-1 the presence of a mutation at codon 74 in combination with a mutation in at least one of codons 65, 69, 70 184, 41, 67, 118, 210, 215, or 219, wherein the presence of such mutations correlates with hypersusceptibility to a NNRTI, thereby determining that the HIV-1 is hypersusceptible to the NNRTI. In certain embodiments, the mutation at codon 74 encodes valine (V). In certain embodiments, a mutation at codon 65 is detected. In certain embodiments, the mutation at codon 65 encodes arginine (R). In certain embodiments, a mutation at codon 69 is detected. In certain embodiments, the mutation at codon 69 encodes alanine (A), aspartic acid (D), asparagine (N), or serine (S). In certain embodiments, the mutation at codon 215 encodes tyrosine (Y). In certain embodiments, the mutation at codon 41 encodes leucine (L). In certain embodiments, the mutation at codon 67 encodes asparagine (N). In certain embodiments, the mutation at codon 70 encodes arginine (R). In certain embodiments, the mutation at codon 210 encodes tryptophan (W). In certain embodiments, the mutation at codon 118 encodes isoleucine (I). In certain embodiments, the mutation at codon 219 encodes glutamic acid (E), histidine H, asparagine (N), glutamine (Q), or arginine (R). In certain embodiments, the NNRTI is EFV, DLV, or NVP. In certain embodiments, the NNRTI is EFV. In certain embodiments, the NNRTI is DLV. In certain embodiments, the NNRTI is NVP.

In yet other embodiments, the method for determining that an HIV-1 is hypersusceptible to a NNRTI comprises detecting in a gene encoding reverse transcriptase of the HIV-1 the presence of a mutation or a combination of mutations significantly associated with NNRTI hypersusceptibility as indicated by Table 2, 3, or 4. In certain embodiments, the significance of the association of the mutation or combination of mutations with NNRTI hypersusceptibility is indicated by an odds ratio less than 1. In certain embodiments, the significance of the association of the mutation or combination of mutations with NNRTI hypersusceptibility is indicated by a p-value calculated in Student's T-Test less than 0.05. In a preferred embodiment, the significance of the association of the mutation or combination of mutations with NNRTI hypersusceptibility is indicated by a p-value calculated in Student's T-Test less than 0.01. In certain embodiments, the NNRTI is EFV, DLV, or NVP. In certain embodiments, the NNRTI is EFV. In certain embodiments, the NNRTI is DLV. In certain embodiments, the NNRTI is NVP.

In another aspect, the methods comprise determining that a subject is infected with an HIV that is hypersusceptible to an NNRTI according to a method of the invention, then advising a medical professional of the treatment option of administering to the subject an effective amount of an NNRTI. In certain embodiments, the NNRTI is EFV, DLV, or NVP.

In another aspect, the methods comprise determining that a subject is infected with an HIV that is hypersusceptible to an NNRTI according to a method of the invention, then advising a medical professional to treat the subject with an effective amount of an NNRTI. In certain embodiments, the NNRTI is EFV, DLV, or NVP.

In still another aspect, the methods comprise determining that a subject is infected with an HIV that is hypersusceptible to an NNRTI according to a method of the invention, and administering to the subject a combination of anti-HIV agents that comprises an effective amount of an NNRTI. In certain embodiments, the NNRTI is EFV, DLV, or NVP.

In still another aspect, the methods comprise determining that a subject is infected with an HIV that is hypersusceptible to an NNRTI according to a method of the invention, then advising a medical professional of the treatment option of administering to the subject a combination of anti-HIV agents that comprises an effective amount of an NNRTI. In certain embodiments, the NNRTI is EFV, DLV, or NVP.

In still another aspect, the methods comprise determining whether a subject is infected with an HIV that is hypersusceptible to an NNRTI according to a method of the invention at a first time, then determining whether the subject remains infected with an HIV that is hypersusceptible to an NNRTI according to a method of the invention at a later second time. In other embodiments, the methods comprise determining whether a subject is infected with an HIV that is hypersusceptible to an NNRTI according to a method of the invention at a first time, then determining whether the subject is infected with an HIV that is no longer hypersusceptible to an NNRTI according to a method of the invention at a later second time.

5.4. Measuring Hypersusceptibility of HIV-1 to an NNRTI

Any method known in the art can be used to determine a viral drug hypersusceptibility phenotype, without limitation. See e.g., U.S. Pat. Nos. 5,837,464 and 6,242,187, each of which is hereby incorporated by reference in its entirety.

In certain embodiments, the phenotypic analysis is performed using recombinant virus assays ("RVAs"). RVAs use virus stocks generated by homologous recombination between viral vectors and viral gene sequences, amplified from the patient virus. In certain embodiments, the viral vector is a HIV vector and the viral gene sequences are protease and/or reverse transcriptase and/or gag sequences.

In preferred embodiments, the phenotypic analysis of NNRTI hypersusceptibility is performed using PHENOSENSE™ (ViroLogic Inc., South San Francisco, Calif.). See Petropoulos et al., 2000, *Antimicrob. Agents Chemother.* 44:920-928; U.S. Pat. Nos. 5,837,464 and 6,242,187. PHENOSENSE™ is a phenotypic assay that achieves the benefits of phenotypic testing and overcomes the drawbacks of previous assays. Because the assay has been automated, PHENOSENSE™ provides high throughput methods under controlled conditions for determining NNRTI resistance, susceptibility, or hypersusceptibility of a large number of individual viral isolates.

The result is an assay that can quickly and accurately define both the replication capacity and the susceptibility profile of a patient's HIV (or other virus) isolates to all currently available antiretroviral drugs, including the NNRTIs EFV, DLV, and NVP. PHENOSENSE™ can obtain results with only one round of viral replication, thereby avoiding selection of subpopulations of virus that can occur during preparation of viral stocks required for assays that rely on fully infectious virus. Further, the results are both quantitative, measuring varying degrees of replication capacity or antiviral resistance or susceptibility, and sensitive, as the test can be performed on blood specimens with a viral load of about 500 copies/mL or above and can detect minority populations of some drug-resistant virus at concentrations of 10% or less of total viral population. Finally, the replication capacity and antiviral drug resistance results are reproducible and can vary by less than about 0.25 logs in about 95% of the assays performed.

PHENOSENSE™ can be used with nucleic acids from amplified viral gene sequences. As discussed below, the nucleic acid can be amplified from any sample known by one of skill in the art to contain a viral gene sequence, without limitation. For example, the sample can be a sample from a human or an animal infected with the virus or a sample from a culture of viral cells. In certain embodiments, the viral sample comprises a genetically modified laboratory strain. In other embodiments, the viral sample comprises a wild-type isolate.

A resistance test vector ("RTV") can then be constructed by incorporating the amplified viral gene sequences into a replication defective viral vector by using any method known in the art of incorporating gene sequences into a vector. In one embodiment, restrictions enzymes and conventional cloning methods are used. See Sambrook et al., 2001, *Molecular Cloning: A Laboratory Manual*, Cold Spring Harbor Laboratory, 3$^{rd}$ ed., NY; and Ausubel et al., 1989, *Current Protocols in Molecular Biology*, Greene Publishing Associates and Wiley Interscience, NY. In a preferred embodiment, ApaI and PinAI restriction enzymes are used. Preferably, the replication defective viral vector is the indicator gene viral vector ("IGVV"). In a preferred embodiment, the viral vector contains a means for detecting replication of the RTV. Preferably, the viral vector contains a luciferase expression cassette.

The assay can be performed by first co-transfecting host cells with RTV DNA and a plasmid that expresses the envelope proteins of another retrovirus, for example, amphotropic murine leukemia virus (MLV). Following transfection, viral particles can be harvested from the cell culture and used to infect fresh target cells in the presence of varying amounts of anti-viral drug(s). The completion of a single round of viral replication in the fresh target cells can be detected by the means for detecting replication contained in the vector. In a preferred embodiment, the completion of a single round of viral replication results in the production of luciferase. By monitoring the amount of, e.g., luciferase activity in the presence of the varying amounts of antiviral drug(s), a resistance curve can be constructed by plotting luciferase activity versus drug concentration. The susceptibility of an HIV, or population of HIV, can be determined by measuring the concentration of antiviral drug at which the luciferase activity detected is half-maximal. This number, the $IC_{50}$, provides a standard and convenient measure of drug resistance.

In preferred embodiments, PHENOSENSE™ is used to evaluate the EFV, DLV, and/or NVP susceptibility phenotype of HIV-1. In other embodiments, PHENOSENSE™ is used to evaluate the EFV, NVP, and/or DLV susceptibility phenotype of HIV-2. In certain embodiments, the HIV-1 strain that is evaluated is a wild-type isolate of HIV-1. In other embodiments, the HIV-1 strain that is evaluated is a mutant strain of HIV-1. In certain embodiments, such mutant strains can be isolated from patients. In other embodiments, the mutant strains can be constructed by site-directed mutagenesis or other equivalent techniques known to one of skill in the art. In still other embodiments, the mutant strains can be isolated from cell culture. The cultures can comprise multiple passages through cell culture in the presence of antiviral compounds to select for mutations that accumulate in culture in the presence of such compounds.

In one embodiment, viral nucleic acid, for example, HIV-1 RNA is extracted from plasma samples, and a fragment of, or entire viral genes can be amplified by methods such as, but not limited to PCR. See, e.g., Hertogs et al., 1998,*Antimicrob Agents Chemother* 42(2):269-76. In one example, a 2.2-kb fragment containing the entire HIV-1 PR- and RT-coding sequence is amplified by nested reverse transcription-PCR. The pool of amplified nucleic acid, for example, the PR-RT-coding sequences, is then cotransfected into a host cell such as CD4+ T lymphocytes (MT4) with the pGEMT3deltaPRT plasmid from which most of the PR (codons 10 to 99) and RT (codons 1 to 482) sequences are deleted. Homologous recombination leads to the generation of chimeric viruses containing viral coding sequences, such as the PR- and RT-coding sequences derived from HIV-1 RNA in plasma. The replication capacities or antiviral drug resistance phenotypes of the chimeric viruses can be determined by any cell viability assay known in the art, and compared to replication capacities or antiviral drug susceptibilities of a statistically significant number of individual viral isolates to assess whether a virus has altered replication capacity or is resistant or hypersusceptible to the antiviral drug. For example, an MT4 cell-3-(4,5-dimethylthiazol-2-yl)-2,5-diphenyltetrazolium bromide-based cell viability assay can be used in an automated system that allows high sample throughput.

In another embodiment, competition assays can be used to assess replication capacity of one viral strain relative to another viral strain. For example, two infectious viral strains can be co-cultivated together in the same culture medium. See, e.g., Lu et al., 2001, *JAIDS* 27:7-13, which is incorporated by reference in its entirety. By monitoring the course of each viral strain's growth, the fitness of one strain relative to the other can be determined. By measuring many viruses' fitness relative to a single reference virus, an objective measure of each strain's fitness can be determined.

Other assays for evaluating the phenotypic susceptibility of a virus to anti-viral drugs known to one of skill in the art can be adapted to determine replication capacity or to determine antiviral drug susceptibility or resistance. See, e.g., Shi and Mellors, 1997, *Antimicrob Agents Chemother.* 41(12):2781-85; Gervaix et al., 1997, *Proc Natl Acad Sci U.S.A.* 94(9):4653-8; Race et al., 1999, *AIDS* 13:2061-2068, incorporated herein by reference in their entireties.

In addition, the phenotypic assays described above can also be used to determine the effectiveness of candidate compounds. Generally, such methods comprise performing the phenotypic assay in the presence and absence of the candidate compound, wherein the difference in activity or expression of the indicator gene indicates the effectiveness of the candidate compound. Advantageously, the methods can be performed in the presence of a mutation associated with NNRTI hypersusceptibility as disclosed herein. By performing such assays in the presence of such mutations, candidate compounds can be identified that have beneficial interactions with the NNRTIs to which the virus is hyper susceptible. In certain embodiments, the candidate compound will have an additive effect on viral inhibition with the NNRTI. In preferred embodiments, the candidate compound will have a synergistic effect on viral inhibition with the NNRTI. Further guidance may be found in performing the assays to determine the effectiveness of candidate compounds in Petropoulos et al., 2000, *Antimicrob. Agents Chemother.* 44:920-928; and U.S. Pat. Nos. 5,837,464 and 6,242,187.

5.4.1. Detecting the Presence or Absence of Mutations in a Virus

The presence or absence of an mutation associated with NNRTI hypersusceptibility according to the present invention in a virus can be determined by any means known in the art for detecting a mutation. The mutation can be detected in the viral gene that encodes a particular protein, or in the protein itself, i.e., in the amino acid sequence of the protein.

In one embodiment, the mutation is in the viral genome. Such a mutation can be in, for example, a gene encoding a viral protein, in a genetic element such as a cis or trans acting regulatory sequence of a gene encoding a viral protein, an intergenic sequence, or an intron sequence. The mutation can affect any aspect of the structure, function, replication or environment of the virus that changes its susceptibility to an anti-viral treatment and/or its replication capacity. In one embodiment, the mutation is in a gene encoding a viral protein that is the target of an currently available anti-viral treatment. In other embodiments, the mutation is in a gene or other genetic element that is not the target of a currently-available anti-viral treatment.

A mutation within a viral gene can be detected by utilizing any suitable technique known to one of skill in the art without limitation. Viral DNA or RNA can be used as the starting point for such assay techniques, and may be isolated according to standard procedures which are well known to those of skill in the art.

The detection of a mutation in specific nucleic acid sequences, such as in a particular region of a viral gene, can be accomplished by a variety of methods including, but not limited to, restriction-fragment-length-polymorphism detection based on allele-specific restriction-endonuclease cleavage (Kan and Dozy, 1978, *Lancet ii:*910-912), mismatch-repair detection (Faham and Cox, 1995, *Genome Res* 5:474-482), binding of MutS protein (Wagner et al., 1995, *Nucl Acids Res* 23:3944-3948), denaturing-gradient gel electrophoresis (Fisher et al., 1983, *Proc. Natl. Acad. Sci. U.S.A.* 80:1579-83), single-strand-conformation-polymorphism detection (Orita et al., 1983, *Genomics* 5:874-879), RNAase cleavage at mismatched base-pairs (Myers et al., 1985, *Science* 230:1242), chemical (Cotton et al., 1988, *Proc. Natl. Acad. Sci. U.S.A.* 85:4397-4401) or enzymatic (Youil et al., 1995, *Proc. Natl. Acad. Sci. U.S.A.* 92:87-91) cleavage of heteroduplex DNA, methods based on oligonucleotide-specific primer extension (Syvänen et al., 1990, *Genomics* 8:684-692), genetic bit analysis (Nikiforov et al., 1994, *Nucl Acids Res* 22:4167-4175), oligonucleotide-ligation assay (Landegren et al., 1988, *Science* 241:1077), oligonucleotide-specific ligation chain reaction ("LCR") (Barrany, 1991, *Proc. Natl. Acad. Sci. U.S.A.* 88:189-193), gap-LCR (Abravaya et al., 1995, *Nucl Acids Res* 23:675-682), radioactive or fluorescent DNA sequencing using standard procedures well known in the art, and peptide nucleic acid (PNA) assays (Orum et al., 1993, *Nucl. Acids Res.* 21:5332-5356; Thiede et al., 1996, *Nucl. Acids Res.* 24:983-984).

In addition, viral DNA or RNA may be used in hybridization or amplification assays to detect abnormalities involving gene structure, including point mutations, insertions, deletions and genomic rearrangements. Such assays may include, but are not limited to, Southern analyses (Southern, 1975, *J. Mol. Biol.* 98:503-517), single stranded conformational polymorphism analyses (SSCP) (Orita et al., 1989, *Proc. Natl. Acad. Sci. USA* 86:2766-2770), and PCR analyses (U.S. Pat. Nos. 4,683,202; 4,683,195; 4,800,159; and 4,965,188; PCR Strategies, 1995 Innis et al. (eds.), Academic Press, Inc.).

Such diagnostic methods for the detection of a gene-specific mutation can involve for example, contacting and incubating the viral nucleic acids with one or more labeled nucleic acid reagents including recombinant DNA molecules, cloned genes or degenerate variants thereof, under conditions favorable for the specific annealing of these reagents to their complementary sequences. Preferably, the lengths of these nucleic acid reagents are at least 15 to 30 nucleotides. After incubation, all non-annealed nucleic acids are removed from the nucleic acid molecule hybrid. The presence of nucleic acids which have hybridized, if any such molecules exist, is then detected. Using such a detection scheme, the nucleic acid from the virus can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining, annealed, labeled nucleic acid reagents is accomplished using standard techniques well-known to those in the art. The gene sequences to which the nucleic acid reagents have annealed can be compared to the annealing pattern expected from a normal gene sequence in order to determine whether a gene mutation is present.

These techniques can easily be adapted to provide high-throughput methods for detecting mutations in viral genomes. For example, a gene array from Affymetrix (Affymetrix, Inc., Sunnyvale, Calif.) can be used to rapidly identify genotypes of a large number of individual viruses. Affymetrix gene arrays, and methods of making and using such arrays, are described in, for example, U.S. Pat. Nos. 6,551,784, 6,548,257, 6,505,125, 6,489,114, 6,451,536, 6,410,229, 6,391,550, 6,379,895, 6,355,432, 6,342,355, 6,333,155, 6,308,170, 6,291,183, 6,287,850, 6,261,776, 6,225,625, 6,197,506, 6,168,948, 6,156,501, 6,141,096, 6,040,138, 6,022,963, 5,919,523, 5,837,832, 5,744,305, 5,834,758, and 5,631,734, each of which is hereby incorporated by reference in its entirety.

In addition, Ausubel et al., eds., *Current Protocols in Molecular Biology*, 2002, Vol. 4, Unit 25B, Ch. 22, which is hereby incorporated by reference in its entirety, provides further guidance on construction and use of a gene array for determining the genotypes of a large number of viral isolates. Finally, U.S. Pat. Nos. 6,670,124; 6,617,112; 6,309,823; 6,284,465; and 5,723,320, each of which is incorporated by reference in its entirety, describe related array technologies that can readily be adapted for rapid identification of a large number of viral genotypes by one of skill in the art.

Alternative diagnostic methods for the detection of gene specific nucleic acid molecules may involve their amplification, e.g., by PCR (U.S. Pat. Nos. 4,683,202; 4,683,195; 4,800,159; and 4,965,188; PCR Strategies, 1995 Innis et al. (eds.), Academic Press, Inc.), followed by the detection of the amplified molecules using techniques well known to those of skill in the art. The resulting amplified sequences can be compared to those which would be expected if the nucleic acid being amplified contained only normal copies of the respective gene in order to determine whether a gene mutation exists.

Additionally, the nucleic acid can be sequenced by any sequencing method known in the art. For example, the viral DNA can be sequenced by the dideoxy method of Sanger et al., 1977, *Proc. Natl. Acad. Sci. USA* 74:5463, as further described by Messing et al., 1981, *Nuc. Acids Res.* 9:309, or by the method of Maxam et al., 1980, *Methods in Enzymology* 65:499. See also the techniques described in Sambrook et al., 2001, *Molecular Cloning: A Laboratory Manual*, Cold Spring Harbor Laboratory, 3$^{rd}$ ed., NY; and Ausubel et al., 1989, *Current Protocols in Molecular Biology*, Greene Publishing Associates and Wiley Interscience, NY.

Antibodies directed against the viral gene products, i.e., viral proteins or viral peptide fragments can also be used to detect mutations in the viral proteins. Alternatively, the viral protein or peptide fragments of interest can be sequenced by any sequencing method known in the art in order to yield the amino acid sequence of the protein of interest. An example of such a method is the Edman degradation method which can be used to sequence small proteins or polypeptides. Larger proteins can be initially cleaved by chemical or enzymatic reagents known in the art, for example, cyanogen bromide, hydroxylamine, trypsin or chymotrypsin, and then sequenced by the Edman degradation method.

5.4.2. Correlating Mutations with Hypersusceptibility to a NNRTI

Any method known in the art can be used to determine whether a mutation is correlated with NNRTI hypersusceptibility. In one embodiment, univariate analysis is used to identify mutations correlated with NNRTI hypersusceptibility. Univariate analysis yields P values that indicate the statistical significance of the correlation. In such embodiments, the smaller the P value, the more significant the measurement. Preferably the P values will be less than 0.05. More preferably, P values will be less than 0.01. Even more preferably, the P value will be less than 0.005. P values can be calculated by any means known to one of skill in the art. In one embodiment, P values are calculated using Fisher's Exact Test. In another embodiment, P values can be calculated with Student's t-test. See, e.g., David Freedman, Robert Pisani & Roger Purves, 1980, Statistics, W. W. Norton, New York. In certain embodiments, P values can be calculated with both Fisher's Exact Test and Student's t-test. In such embodiments, P values calculated with both tests are preferably less than 0.05. However, a correlation with a P value that is less than 0.10 in one test but less than 0.05 in another test can still be considered to be a marginally significant correlation. Such mutations are suitable for further analysis with, for example, multivariate analysis. Alternatively, further univariate analysis can be performed on a larger sample set to confirm the significance of the correlation.

Further, an odds ratio can be calculated to determine whether a mutation correlates with hypersusceptibility to a NNRTI. Generally, calculation of odds rations depends on dividing the percentage of virus that comprise a particular mutation or mutations that are identified as not hypersusceptible to a NNRTI by the percentage of virus with the same mutation or mutations that are identified as hypersusceptible to the NNRTI. In certain embodiments, an odds ratio that is greater than one indicates that the mutation does not correlate with hypersusceptibility to a NNRTI. In certain embodiments, an odds ratio that is less than one indicates that the mutation correlates with hypersusceptibility to a NNRTI.

In yet another embodiment, multivariate analysis can be used to determine whether a mutation correlates with NNRTI hypersusceptibility. Any multivariate analysis known by one of skill in the art to be useful in calculating such a correlation can be used, without limitation. In certain embodiments, a statistically significant number of virus's resistance or susceptibility phenotypes, e.g., $IC_{50}$, can be determined. These $IC_{50}$ values can then be divided into groups that correspond to percentiles of the set of $IC_{50}$ values observed.

After assigning each virus's $IC_{50}$ value to the appropriate group, the genotype of that virus can be assigned to that group. By performing this method for all viral isolates, the number of instances of a particular mutation in a given percentile of NNRTI susceptibility can be observed. This allows the skilled practitioner to identify mutations that correlate with NNRTI hypersusceptibility.

Finally, in yet another embodiment, regression analysis can be performed to identify mutations that best predict NNRTI hypersusceptibility. In such embodiments, regression analysis is performed on a statistically significant number of viral isolates for which genotypes and NNRTI susceptibility phenotypes have been determined. The analysis then identifies which mutations appear to best predict, e.g., most strongly correlate with, NNRTI hypersusceptibility. Such analysis can then be used to construct rules for predicting NNRTI hypersusceptibility based upon knowledge of the genotype of a particular virus, described below. In certain embodiments, software such as, for example, CART 5.0, Prism 4.0, or Insightful Miner 3.0 can be used to perform the analysis that identifies the mutations that appear to best predict NNRTI hypersusceptibility.

5.4.3. Computer-Implemented Methods for Determining Hypersusceptibility to a NNRTI, and Articles Related Thereto In another aspect, the present invention provides computer-implemented methods for determining that an HIV-1 is hypersusceptible to a NNRTI. In such embodiments, the methods of the invention are adapted to take advantage of the processing power of modern computers. One of skill in the art can readily adapt the methods in such a manner.

Therefore, in certain embodiments, the invention provides a computer-implemented method for determining that an HIV-1 is hypersusceptible to a NNRTI, comprising inputting genetic information into a memory system of a computer, wherein the genetic information indicates that the HIV-1 has a gene encoding reverse transcriptase with a mutation at codon 65 or 69, inputting a correlation between the presence of the mutations and hypersusceptibility to a NNRTI into the memory system of the computer, and determining that the HIV-1 is hypersusceptible to the NNRTI. In certain embodiments, the genetic information indicates that the HIV-1 has a mutation at codon 65. In certain embodiments, the genetic information indicates that the mutation at codon 65 encodes arginine (R). In certain embodiments, the genetic information indicates that the HIV-1 has a mutation at codon 69. In certain embodiments, the mutation at codon 69 encodes alanine (A), aspartic acid (D), asparagine (N), or serine (S). In certain embodiments, the NNRTI is EFV, DLV, or NVP. In certain embodiments, the NNRTI is EFV. In certain embodiments, the NNRTI is DLV. In certain embodiments, the NNRTI is NVP.

In certain embodiments, the genetic information further indicates that the HIV-1 has a gene encoding reverse transcriptase with a mutation at codon 184 in addition to codon 65 or 69. In certain embodiments, the genetic information indicates that the mutation at codon 184 encodes valine (V).

In certain embodiments, the invention provides a computer-implemented method for determining that an HIV-1 is hypersusceptible to a NNRTI, comprising inputting genetic information into a memory system of a computer, wherein the genetic information indicates that the HIV-1 has a gene encoding reverse transcriptase with a mutation at codon 70 in combination with mutations in at least two of codons 41, 67, 210, 215, and 219, inputting a correlation between the presence of the mutations and hypersusceptibility to a NNRTI into the memory system of the computer, and determining that the HIV-1 is hypersusceptible to the NNRTI. In certain embodiments, the genetic information indicates that the mutation at codon 70 encodes arginine (R). In certain embodiments, the genetic information indicates that the HIV-1 has a mutation at codon 41. In certain embodiments, the genetic information indicates that the mutation at codon 41 encodes leucine (L). In certain embodiments, the genetic information indicates that the HIV-1 has a mutation at codon 67. In certain embodiments, the genetic information indicates that the mutation at codon 67 encodes asparagine (N). In certain embodiments, the genetic information indicates that the HIV-1 has a mutation at codon 210. In certain embodiments, the genetic information indicates that the mutation at codon 210 encodes tryptophan (W). In certain embodiments, the genetic information indicates that the HIV-1 has a mutation at codon 215. In certain embodiments, the genetic information indicates that the mutation at codon 215 encodes tyrosine (Y). In certain embodiments, the genetic information indicates that the HIV-1 has a mutation at codon 219. In certain embodiments, the mutation at codon 219 encodes glutamic acid (E), histidine H, asparagine (N), glutamine (Q), or arginine (R). In certain embodiments, the NNRTI is EFV, DLV, or NVP. In certain embodiments, the NNRTI is EFV. In certain embodiments, the NNRTI is DLV. In certain embodiments, the NNRTI is NVP.

In certain embodiments, the genetic information further indicates that the HIV-1 has a gene encoding reverse transcriptase with a mutation at codon 118. In certain embodiments, the genetic information indicates that the mutation at codon 118 encodes isoleucine (I).

In certain embodiments, the invention provides a computer-implemented method for determining that an HIV-1 is hypersusceptible to a NNRTI, comprising inputting genetic information into a memory system of a computer, wherein the genetic information indicates that the HIV-1 has a gene encoding reverse transcriptase with a mutation at codon 74, inputting a correlation between the presence of the mutations and hypersusceptibility to a NNRTI into the memory system of the computer, and determining that the HIV-1 is hypersusceptible to the NNRTI. In certain embodiments, the genetic information indicates that the mutation at codon 74 encodes valine (V). In certain embodiments, the NNRTI is EFV, DLV, or NVP. In certain embodiments, the NNRTI is EFV. In certain embodiments, the NNRTI is DLV. In certain embodiments, the NNRTI is NVP.

In certain embodiments, the methods further comprise displaying that the HIV-1 is hypersusceptible to a NNRTI on a display of the computer. In certain embodiments, the methods further comprise printing that the HIV-1 is hypersusceptible to a NNRTI.

In another aspect, the invention provides a tangible medium comprising data indicating that an HIV-1 is hypersusceptible to an NNRTI because of the presence of one or more mutations correlated with NNRTI hypersusceptibility as disclosed herein. In certain embodiments, the tangible medium is a paper document indicating that an HIV-1 is hypersusceptible to a NNRTI. In certain embodiments, the paper document is a printed document, e.g., a computer print-out. In certain embodiments, the tangible medium is a computer-readable medium comprising data indicating that an HIV-1 is hypersusceptible to a NNRTI. In certain embodiments, the computer-readable medium is a random-access memory. In certain embodiments, the computer-readable medium is a fixed disk. In certain embodiments, the computer-readable medium is a floppy disk. In certain embodiments, the computer-readable medium is a portable memory device, such as, e.g., a USB key or an iPod™.

In still another aspect, the invention provides an article of manufacture that comprises computer-readable instructions for performing a method of the invention. In certain embodiments, the article of manufacture is a random-access memory. In certain embodiments, the article of manufacture is a fixed disk. In certain embodiments, the article of manufacture is a floppy disk. In certain embodiments, the article of manufacture is a portable memory device, such as, e.g., a USB key or an iPod™.

In yet another aspect, the invention provides a computer-readable medium that comprises data indicating that an HIV-1 is hypersusceptible to a NNRTI as determined by a method of the invention and computer-readable instructions for performing a method of the invention. In certain embodiments, the computer-readable medium is a random-access memory. In certain embodiments, the computer-readable medium is a fixed disk. In certain embodiments, the computer-readable medium is a floppy disk. In certain embodiments, the computer-readable medium is a portable memory device, such as, e.g., a USB key or an iPod™.

In yet another aspect, the invention provides a computer system that is configured to perform a method of the invention.

5.4.4. Viruses and Viral Samples

A mutation associated with NNRTI hypersusceptibility according to the present invention can be present in any type of virus. For example, such mutations may be identified in any virus that infects animals known to one of skill in the art without limitation. In one embodiment of the invention, the virus includes viruses known to infect mammals, including dogs, cats, horses, sheep, cows etc. In certain embodiment, the virus is known to infect primates. In preferred embodiments, the virus is known to infect humans. Examples of such viruses that infect humans include, but are not limited to, human immunodeficiency virus ("HIV"), herpes simplex virus, cytomegalovirus virus, varicella zoster virus, other human herpes viruses, influenza A, B and C virus, respiratory syncytial virus, hepatitis A, B and C viruses, rhinovirus, and human papilloma virus. In certain embodiments, the virus is HCV. In other embodiments, the virus is HBV. In a preferred embodiment of the invention, the virus is HIV. Even more preferably, the virus is human immunodeficiency virus type 1 ("HIV-1"). The foregoing are representative of certain viruses for which there is presently available anti-viral chemotherapy and represent the viral families retroviridae, herpesviridae, orthomyxoviridae, paramyxoviridae, picornaviridae, flaviviridae, pneumoviridae and hepadnaviridae. This invention can be used with other viral infections due to other viruses within these families as well as viral infections arising from viruses in other viral families for which there is or there is not a currently available therapy.

A mutation associated with NNRTI hypersusceptibility according to the present invention can be found in a viral sample obtained by any means known in the art for obtaining viral samples. Such methods include, but are not limited to, obtaining a viral sample from a human or an animal infected with the virus or obtaining a viral sample from a viral culture. In one embodiment, the viral sample is obtained from a human individual infected with the virus. The viral sample could be obtained from any part of the infected individual's body or any secretion expected to contain the virus. Examples of such parts include, but are not limited to blood, serum, plasma, sputum, lymphatic fluid, semen, vaginal mucus and samples of other bodily fluids. In a preferred embodiment, the sample is a blood, serum or plasma sample.

In another embodiment, a mutation associated with NNRTI hypersusceptibility according to the present invention is present in a virus that can be obtained from a culture. In some embodiments, the culture can be obtained from a laboratory. In other embodiments, the culture can be obtained from a collection, for example, the American Type Culture Collection.

In certain embodiments, a mutation associated with NNRTI hypersusceptibility according to the present invention is present in a derivative of a virus. In one embodiment, the derivative of the virus is not itself pathogenic. In another embodiment, the derivative of the virus is a plasmid-based system, wherein replication of the plasmid or of a cell transfected with the plasmid is affected by the presence or absence of the selective pressure, such that mutations are selected that increase resistance to the selective pressure. In some embodiments, the derivative of the virus comprises the nucleic acids or proteins of interest, for example, those nucleic acids or proteins to be targeted by an anti-viral treatment. In one embodiment, the genes of interest can be incorporated into a vector. See, e.g., U.S. Pat. Nos. 5,837,464 and 6,242,187 and PCT publication, WO 99/67427, each of which is incorporated herein by reference. In certain embodiments, the genes can be those that encode for a protease or reverse transcriptase.

In another embodiment, the intact virus need not be used. Instead, a part of the virus incorporated into a vector can be used. Preferably that part of the virus is used that is targeted by an anti-viral drug.

In another embodiment, a mutation associated with NNRTI hypersusceptibility according to the present invention is present in a genetically modified virus. The virus can be genetically modified using any method known in the art for genetically modifying a virus. For example, the virus can be grown for a desired number of generations in a laboratory culture. In one embodiment, no selective pressure is applied (i.e., the virus is not subjected to a treatment that favors the replication of viruses with certain characteristics), and new mutations accumulate through random genetic drift. In another embodiment, a selective pressure is applied to the virus as it is grown in culture (i.e., the virus is grown under conditions that favor the replication of viruses having one or more characteristics). In one embodiment, the selective pressure is an anti-viral treatment. Any known anti-viral treatment can be used as the selective pressure.

In certain embodiments, the virus is HIV and the selective pressure is a NNRTI. In another embodiment, the virus is HIV-1 and the selective pressure is a NNRTI. Any NNRTI can be used to apply the selective pressure. Examples of NNRTIs include, but are not limited to, nevirapine, delavirdine and efavirenz. By treating HIV cultured in vitro with a NNRTI, one can select for mutant strains of HIV that have an increased resistance to the NNRTI. The stringency of the selective pressure can be manipulated to increase or decrease the survival of viruses not having the selected-for characteristic.

In other embodiments, the virus is HIV and the selective pressure is a NRTI. In another embodiment, the virus is HIV-1 and the selective pressure is a NRTI. Any NRTI can be used to apply the selective pressure. Examples of NRTIs include, but are not limited to, AZT, ddI, ddC, d4T, 3TC, abacavir, and tenofovir. By treating HIV cultured in vitro with a NRTI, one can select for mutant strains of HIV that have an increased resistance to the NRTI. The stringency of the selective pressure can be manipulated to increase or decrease the survival of viruses not having the selected-for characteristic.

In still other embodiments, the virus is HIV and the selective pressure is a PI. In another embodiment, the virus is HIV-1 and the selective pressure is a PI. Any PI can be used to apply the selective pressure. Examples of PIs include, but are not limited to, saquinavir, ritonavir, indinavir, nelfinavir, amprenavir, lopinavir and atazanavir. By treating HIV cultured in vitro with a PI, one can select for mutant strains of HIV that have an increased resistance to the PI. The stringency of the selective pressure can be manipulated to increase or decrease the survival of viruses not having the selected-for characteristic.

In still other embodiments, the virus is HIV and the selective pressure is an entry inhibitor. In another embodiment, the virus is HIV-1 and the selective pressure is an entry inhibitor. Any entry inhibitor can be used to apply the selective pressure. An example of a entry inhibitor includes, but is not limited to, fusion inhibitors such as, for example, enfuvirtide. Other entry inhibitors include co-receptor inhibitors, such as, for example, AMD3100 (Anormed). Such co-receptor inhibitors can include any compound that interferes with an interaction between HIV and a co-receptor, e.g., CCR5 or CRCX4, without limitation. By treating HIV cultured in vitro with an entry inhibitor, one can select for mutant strains of HIV that have an increased resistance to the entry inhibitor. The stringency of the selective pressure can be manipulated to increase or decrease the survival of viruses not having the selected-for characteristic.

In another aspect, a mutation associated with NNRTI hypersusceptibility according to the present invention can be made by mutagenizing a virus, a viral genome, or a part of a viral genome. Any method of mutagenesis known in the art can be used for this purpose. In certain embodiments, the mutagenesis is essentially random. In certain embodiments, the essentially random mutagenesis is performed by exposing the virus, viral genome or part of the viral genome to a mutagenic treatment. In another embodiment, a gene that encodes a viral protein that is the target of an anti-viral therapy is mutagenized. Examples of essentially random mutagenic treatments include, for example, exposure to mutagenic substances (e.g., ethidium bromide, ethylmethanesulphonate, ethyl nitroso urea (ENU) etc.) radiation (e.g., ultraviolet light), the insertion and/or removal of transposable elements (e.g., Tn5, Tn10), or replication in a cell, cell extract, or in vitro replication system that has an increased rate of mutagenesis. See, e.g., Russell et al., 1979, *Proc. Nat. Acad. Sci. USA* 76:5918-5922; Russell, W., 1982, Environmental Mutagens and Carcinogens: Proceedings of the Third International Conference on Environmental Mutagens. One of skill in the art will appreciate that while each of these methods of mutagenesis is essentially random, at a molecular level, each has its own preferred targets.

In another aspect, a mutation associated with NNRTI hypersusceptibility can be made using site-directed mutagenesis. Any method of site-directed mutagenesis known in the art can be used (see e.g., Sambrook et al., 2001, *Molecular Cloning: A Laboratory Manual*, Cold Spring Harbor Laboratory, 3$^{rd}$ ed., NY; and Ausubel et al., 1989, *Current Protocols in Molecular Biology*, Greene Publishing Associates and Wiley Interscience, NY). See, e.g., Sarkar and Sommer, 1990, *Biotechniques*, 8:404-407. The site directed mutagenesis can be directed to, e.g., a particular gene or genomic region, a particular part of a gene or genomic region, or one or a few particular nucleotides within a gene or genomic region. In one embodiment, the site directed mutagenesis is directed to a viral genomic region, gene, gene fragment, or nucleotide based on one or more criteria. In one embodiment, a gene or a portion of a gene is subjected to site-directed mutagenesis because it encodes a protein that is known or suspected to be a target of an anti-viral therapy, e.g., the gene encoding the HIV reverse transcriptase. In another embodiment, a portion of a gene, or one or a few nucleotides within a gene, are selected for site-directed mutagenesis. In one embodiment, the nucleotides to be mutagenized encode amino acid residues that are known or suspected to interact with an anti-viral compound. In another embodiment, the nucleotides to be mutagenized encode amino acid residues that are known or suspected to be mutated in viral strains that are resistant or susceptible or hypersusceptible to one or more antiviral agents. In another embodiment, the mutagenized nucleotides encode amino acid residues that are adjacent to or near in the primary sequence of the protein residues known or suspected to interact with an anti-viral compound or known or suspected to be mutated in viral strains that are resistant or susceptible or hypersusceptible to one or more antiviral agents. In another embodiment, the mutagenized nucleotides encode amino acid residues that are adjacent to or near to in the secondary, tertiary or quaternary structure of the protein residues known or suspected to interact with an anti-viral compound or known or suspected to be mutated in viral strains having an altered replication capacity. In another embodiment, the mutagenized nucleotides encode amino acid residues in or near the active site of a protein that is known or suspected to bind to an anti-viral compound.

6. EXAMPLES

6.1. Example 1: Measuring NNRTI Hypersusceptibility Using Resistance Test Vectors This example provides methods and compositions for accurately and reproducibly measuring the resistance or sensitivity of HIV-1 to antiretroviral drugs including, for example, NNRTIs such as EFV, DLV, and/or NVP. The methods for measuring resistance or susceptibility to such drugs can be adapted to other HIV strains, such as HIV-2, or to other viruses, including, but not limited to hepadnaviruses (e.g., human hepatitis B virus), flaviviruses (e.g., human hepatitis C virus) and herpesviruses (e.g., human cytomegalovirus).

Drug resistance tests can be carried out, for example, using the methods for phenotypic drug susceptibility and resistance tests described in U.S. Pat. No. 5,837,464 (International Publication Number WO 97/27319) which is hereby incorporated by reference in its entirety, or according to the protocol that follows.

Patient-derived segment(s) corresponding to the HIV protease and reverse transcriptase coding regions were amplified by the reverse transcription-polymerase chain reaction method (RT-PCR) using viral RNA isolated from viral particles present in the plasma or serum of HIV-infected individuals as follows. Viral RNA was isolated from the plasma or serum using oligo-dT magnetic beads (Dynal Biotech, Oslo, Norway), followed by washing and elution of viral RNA. The RT-PCR protocol was divided into two steps. A retroviral reverse transcriptase (e.g. Moloney MuLV reverse transcriptase (Roche Molecular Systems, Inc., Branchburg, N.J.; Invitrogen, Carlsbad, Calif.), or avian myeloblastosis virus (AMV) reverse transcriptase, (Boehringer Mannheim, Indianapolis, Ind.), or) was used to copy viral RNA into cDNA. The cDNA was then amplified using a thermostable DNA polymerase (e.g. Taq (Roche Molecular Systems, Inc., Branchburg, N.J.), Tth (Roche Molecular Systems, Inc., Branchburg, N.J.), PRIMEZYMET™ (isolated from *Thermus brockianus*, Biometra, Gottingen, Germany)) or a combination of thermostable polymerases as described for the performance of "long PCR" (Barnes, W. M., 1994, Proc. Natl. Acad. Sci, USA 91, 2216-20) (e.g. Expand High Fidelity PCR System (Taq+Pwo), (Boehringer Mannheim. Indianapolis, Ind.); GENEAMP XL™ PCR kit (Tth+Vent), (Roche Molecular Systems, Inc., Branchburg, N.J.); or ADVANTAGE II®, Clontech, Palo Alto, Calif.) PCR primers were designed to introduce ApaI and PinA1 recognition sites into the 5' or 3' end of the PCR product, respectively.

Resistance test vectors incorporating the "test" patient-derived segments were constructed as described in U.S. Pat. No. 5,837,464 using an amplified DNA product of 1.5 kB prepared by RT-PCR using viral RNA as a template and oligonucleotides PDS Apa, PDS Age, PDS PCR6, Apa-gen, Apa-c, Apa-f, Age-gen, Age-a, RT-ad, RT-b, RT-c, RT-f, and/or RT-g as primers, followed by digestion with ApaI and AgeI or the isoschizomer PinA1. To ensure that the plasmid DNA corresponding to the resultant fitness test vector comprises a representative sample of the HIV viral quasi-species present in the serum of a given patient, many (>250) independent *E. coli* transformants obtained in the construction of a given fitness test vector are pooled and used for the preparation of plasmid DNA.

A packaging expression vector encoding an amphotrophic MuLV 4070A env gene product enables production in a resistance test vector host cell of resistance test vector viral particles which can efficiently infect human target cells. Resistance test vectors encoding all HIV genes with the exception of env were used to transfect a packaging host cell (once transfected the host cell is referred to as a fitness test vector host cell). The packaging expression vector which encodes the amphotrophic MuLV 4070A env gene product is used with the resistance test vector to enable production in the resistance test vector host cell of infectious pseudotyped resistance test vector viral particles.

Drug resistance tests performed with resistance test vectors were carried out using packaging host and target host cells consisting of the human embryonic kidney cell line 293.

Resistance tests were carried out with resistance test vectors using two host cell types. Resistance test vector viral particles were produced by a first host cell (the resistance test vector host cell) that was prepared by transfecting a packaging host cell with the resistance test vector and the packaging expression vector. The resistance test vector viral particles were then used to infect a second host cell (the target host cell) in which the expression of the indicator gene is measured.

The resistance test vectors containing a functional luciferase gene cassette were constructed as described above and host cells were transfected with the resistance test vector DNA. The resistance test vectors contained patient-derived reverse transcriptase and protease DNA sequences that encode proteins which were either susceptible or resistant to the antiretroviral agents, such as, for example, NRTIs, NNRTIs, and PIs.

The amount of luciferase activity detected in infected cells is used as a direct measure of "infectivity," i.e., the ability of the virus to complete a single round of replication. Thus, drug resistance or sensitivity can be determined by plotting the amount of luciferase activity produced by patient derived viruses in the presence of varying concentrations of the antiviral drug. By identifying the concentration of drug at which luciferase activity is half-maximum, the $IC_{50}$ of the virus from which patient-derived segments) were obtained for the antiretroviral agent can be determined.

Host (293) cells were seeded in 10-cm-diameter dishes and were transfected one day after plating with resistance test vector plasmid DNA and the envelope expression vector. Transfections were performed using a calcium-phosphate co-precipitation procedure. The cell culture media containing the DNA precipitate was replaced with fresh medium, from one to 24 hours, after transfection. Cell culture medium containing resistance test vector viral particles was harvested one to four days after transfection and was passed through a 0.45-mm filter before optional storage at −80° C. Before infection, target cells (293 cells) were plated in cell culture media. Control infections were performed using cell culture media from mock transfections (no DNA) or transfections containing the resistance test vector plasmid DNA without the envelope expression plasmid. One to three or more days after infection the media was removed and cell lysis buffer (Promega Corp.; Madison, Wis.) was added to each well. Cell lysates were assayed for luciferase activity. Alternatively, cells were lysed and luciferase was measured by adding Steady-Glo (Promega Corp.; Madison, Wis.) reagent directly to each well without aspirating the culture media from the well. The amount of luciferase activity produced in infected cells was normalized to adjust for variation in transfection efficiency in the transfected host cells by measuring the luciferase activity in the transfected cells, which is not dependent on viral gene functions, and adjusting the luciferase activity from infected cell accordingly.

6.2. Example 2: Identifying Mutations Correlated with Hypersusceptibility to a NNRTI This example provides methods and compositions for identifying mutations that correlate with hypersusceptibility to a NNRTI. Resistance test vectors were constructed and used as described in Example 1. Resistance test vectors derived from patient samples or clones derived from the resistance test vector pools were tested in a resistance assay to determine accurately and quantitatively the relative EFV, DLV, or NVP resistance or susceptibility compared to the median observed resistance or susceptibility.

Genotypic Analysis of Patient HIV Samples:

Resistance test vector DNAs, either pools or clones, can be analyzed by any genotyping method, e.g., as described above. In this example, patient HIV sample sequences were determined using viral RNA purification, RT/PCR and ABI chain terminator automated sequencing. The sequence that was determined was compared to that of a reference sequence, NLA4-3. The genotype was examined for sequences that were different from the reference or pre-treatment sequence and correlated to the observed $IC_{50}$ for EFV, NVP, and DLV.

Correlation of Mutations with Hypersusceptibility to a NNRTI:

To identify mutations associated with NNRTI hypersusceptibility, the following analysis was performed. A collection of 2019 samples that comprise the one of several NRTI resistance mutations, including K65R, T69X, L74IV, V75X, M184IV, but do not comprise the Q151M, T69ins, or NNRTI resistance mutations A98G, L100I, K101EP, K103NS, V106AM, Y181X, Y188X, G190C, P225X, F227X, M230L, or P236L were identified and their EFV, DLV, and NVP susceptibility phenotypes were determined as described above. Viruses that exhibit an $IC_{50}$ 0.4 fold lower than wild-type virus were designated as hypersusceptible to the respective NNRTI. The distribution of such viruses in the dataset is presented in Table 1, below. The TAMs referenced in Table 1 include M41L, D67N, K70R, L210W, T215FY, and K219X, while the NAMs referenced include K65R, T69X, L74IV, V75X, and M184IV. Isolates without NRTI, NNRTI or PI mutations served as a wild type (WT) reference group. Further comparison groups comprised isolates with three TAMS including T215Y (+/−H208Y, +/−V118I) or three TAMS including K70R. Scatter plots and statistical tests (See FIGS. 1-6) were generated using Prism 4.0 (GraphPad, San Diego, Calif.)

TABLE 1

| RT Mutations | Number of samples | $IC_{50}$ EFV | | | |
|---|---|---|---|---|---|
| | | Mean $IC_{50}$ | Median $IC_{50}$ | Min-Max $IC_{50}$ | % $IC_{50}$ 0.4 fold < WT |
| None | 10090 | 1.0 | 0.9 | 0.1-21.9 | 4.2% |
| 1 NAM | 1847 | 0.7 | 0.6 | 0.1-6.8 | 17.8% |
| 2 NAMs | 133 | 0.5 | 0.5 | 0.1-2.6 | 39.8% |
| 3 NAMs | 39 | 0.6 | 0.5 | 0.2-1.9 | 28.2% |
| 65R | 36 | 0.5 | 0.4 | 0.2-2.3 | 47.2% |
| 184V | 1666 | 0.7 | 0.6 | 0.1-6.8 | 16.9% |
| 69X | 106 | 0.8 | 0.7 | 0.2-4.8 | 19.8% |
| 65R and 184V | 75 | 0.4 | 0.4 | 0.2-1.2 | 54.7% |
| T215Y and 2 TAMs | 80 | 0.4 | 0.4 | 0.1-1.3 | 55.0% |
| T215Y and 2 TAMs and H208X | 11 | 0.4 | 0.3 | 0.2-0.5 | 54.5% |
| T215Y and 2 TAMs and H208 wt | 69 | 0.4 | 0.4 | 0.1-1.3 | 55.1% |
| K70R and 2 TAMs | 84 | 0.7 | 0.5 | 0.2-4.2 | 31.0% |
| T215Y and 2 TAMs and V118I | 48 | 0.5 | 0.4 | 0.1-1.2 | 39.6% |
| T215Y and 2 TAMs and V118 wt | 32 | 0.4 | 0.3 | 0.1-1.3 | 78.1% |

TABLE 1-continued

| RT Mutations | Number of samples | IC$_{50}$ NVP | | | |
|---|---|---|---|---|---|
| | | Mean IC$_{50}$ | Median IC$_{50}$ | Min-Max IC$_{50}$ | % IC$_{50}$ 0.4 fold < WT |
| None | 10090 | 1.1 | 0.9 | 0.1-52.7 | 8.1% |
| 1 NAM | 1847 | 0.9 | 0.7 | 0.1-34.1 | 18.0% |
| 2 NAMs | 133 | 0.6 | 0.5 | 0.1-3.1 | 39.8% |
| 3 NAMs | 39 | 0.7 | 0.6 | 0.2-1.9 | 17.9% |
| 65R | 36 | 0.5 | 0.4 | 0.1-3.5 | 55.6% |
| 184V | 1666 | 0.9 | 0.7 | 0.1-34.1 | 16.3% |
| 69X | 106 | 0.9 | 0.7 | 0.1-10.2 | 20.8% |
| 65R and 184V | 75 | 0.5 | 0.4 | 0.1-2.4 | 50.7% |
| T215Y and 2 TAMs | 80 | 0.7 | 0.5 | 0.2-4.4 | 31.3% |
| T215Y and 2 TAMs and H208X | 11 | 0.6 | 0.6 | 0.4-0.9 | 9.1% |
| T215Y and 2 TAMs and H208 wt | 69 | 0.7 | 0.5 | 0.2-4.4 | 34.8% |
| K70R and 2 TAMs | 84 | 0.8 | 0.5 | 0.1-8 | 36.9% |
| T215Y and 2 TAMs and V118I | 48 | 0.7 | 0.7 | 0.2-1.5 | 27.1% |
| T215Y and 2 TAMs and V118 wt | 32 | 0.7 | 0.5 | 0.2-4.4 | 37.5% |

| RT Mutations | Number of samples | IC$_{50}$ DLV | | | |
|---|---|---|---|---|---|
| | | Mean IC$_{50}$ | Median IC$_{50}$ | Min-Max IC$_{50}$ | % IC$_{50}$ 0.4 fold < WT |
| None | 10090 | 1.4 | 1.2 | 0-79 | 4.9% |
| 1 NAM | 1847 | 1.1 | 0.8 | 0-29.4 | 13.2% |
| 2 NAMs | 133 | 0.8 | 0.6 | 0.1-5.1 | 30.1% |
| 3 NAMs | 39 | 0.8 | 0.6 | 0.1-3 | 12.8% |
| 65R | 36 | 0.7 | 0.5 | 0.1-3.4 | 44.4% |
| 184V | 1666 | 1.1 | 0.8 | 0.1-29.4 | 12.3% |
| 69X | 106 | 1.2 | 0.9 | 0.1-10.8 | 13.2% |
| 65R and 184V | 75 | 0.6 | 0.5 | 0.1-1.9 | 42.7% |
| T215Y and 2 TAMs | 80 | 0.4 | 0.3 | 0.1-4 | 71.8% |
| T215Y and 2 TAMs and H208X | 11 | 0.3 | 0.3 | 0.2-0.4 | 90.9% |
| T215Y and 2 TAMs and H208 wt | 69 | 0.4 | 0.3 | 0.1-4 | 68.7% |
| K70R and 2 TAMs | 84 | 1.6 | 0.8 | 0.1-32.2 | 15.7% |
| T215Y and 2 TAMs and V118I | 48 | 0.4 | 0.3 | 0.1-0.9 | 63.8% |
| T215Y and 2 TAMs and V118 wt | 32 | 0.4 | 0.2 | 0.1-4 | 83.9% |

Mutations Associated with NNRTI Hypersusceptibility

The experiments described above identified a number of mutations that significantly correlate with hypersusceptibility to a NNRTI. The specific mutations identified as most significantly correlated with NNRTI hypersusceptibility are presented in Table 1, above.

Compared to the WT population, the mean EFV, DLV, or NVP fold change (FC) was significantly lower in all groups containing NAMs or the combination of TAMs shown in Table 1, with $p<0.0001$ as determined by Student's T-test using the Prism 4.0 software. In addition, a pairwise comparison between two sets of data was conducted using Bonferroni's Multiple Comparison Test using the Prism 4.0 software. The results of the comparison are presented in Tables 2, 3, and 4, appended to the end of this document. Samples with K65R, K65R+M184V, or 2 TAMs in combination with T215Y had over 40% with EFV FC<0.4. Comparisons between samples with 2 TAMs in combination with T215Y+/−H208Y were not significant for any NNRTI; the NNRTI FC in samples with 2 TAMs in combination with T215Y and with V118I was marginally significantly lower than samples without V118I ($p=0.048$).

In addition, NNRTI susceptibilities were measured in site-directed mutants (SDMs) in an NL4-3 background (FIGS. 4 and 5). SDMs bearing only K65R had FC for EFV, NVP and DLV of 0.56+/−0.02, 0.53+/−0.05 and 0.54+/−0.03, respectively (mean+/−SD of 18 replicates, $p<0.00001$ versus reference). SDMs bearing only M184V had FC for EFV, NVP and DLV of 0.65+/−0.03, 0.67+/−0.05 and 0.65+/−0.05, respectively (mean+/−SD of 17 replicates, $p<0.00001$ versus reference). Although discrete, the differences in FC for K65R and M184V were significant ($p<0.00001$). These data highlight the high reproducibility of the PhenoSense™ assay, while the juxtaposed data from clinical isolates emphasize the much broader range of phenotypic susceptibilities encountered in clinical isolates with the same resistance mutations (FIGS. 1-3 and 6).

Further, a SDM in an NL4-3 background was constructed to assess the impact of a mutation at codon 74 or HIV reverse transcriptase. SDMs containing the L74V mutation in reverse transcriptase exhibited a FC for EFV, NVP, and DLV of 0.67+/−0.02, 0.59+/−0.06, and 0.68+/−0.06, respectively, relative to NL4-3.

All references cited herein are incorporated by reference in their entireties.

The examples provided herein, both actual and prophetic, are merely embodiments of the present invention and are not intended to limit the invention in any way.

TABLE 2

Bonferroni's Multiple Comparison Test - EFV Hypersusceptibility

| Values Compared | Mean Diff. | t | P value | 95% CI of diff |
|---|---|---|---|---|
| wt vs 1 NAM | 0.2652 | 20.91 | P < 0.001 | 0.2213 to 0.3090 |
| wt vs 2 NAMs | 0.4373 | 9.998 | P < 0.001 | 0.2862 to 0.5885 |
| wt vs 3 NAMs | 0.3908 | 4.86 | P < 0.001 | 0.1129 to 0.6687 |
| wt vs K65R | 0.4217 | 5.04 | P < 0.001 | 0.1325 to 0.7109 |
| wt vs M184V | 0.2668 | 20.13 | P < 0.001 | 0.2210 to 0.3126 |
| wt vs T69 | 0.1698 | 3.471 | P < 0.05 | 0.0007152 to 0.3389 |
| wt vs K65R + M184V | 0.5346 | 9.204 | P < 0.001 | 0.3338 to 0.7353 |
| wt vs T215Y_3_TAMs | 0.5303 | 9.427 | P < 0.001 | 0.3359 to 0.7247 |
| wt vs T215Y_3_TAMs_208 | 0.5946 | 3.933 | P < 0.01 | 0.07209 to 1.117 |
| wt vs T215Y_3_TAMs_no208 | 0.5201 | 8.591 | P < 0.001 | 0.3108 to 0.7293 |
| wt vs K70R_3_TAMs | 0.2374 | 4.323 | P < 0.01 | 0.04762 to 0.4272 |
| wt vs T215Y_3_TAMs_no118 | 0.4877 | 6.726 | P < 0.001 | 0.2371 to 0.7383 |
| Wt vs T215Y_3_TAMs_118 | 0.5942 | 6.697 | P < 0.001 | 0.2876 to 0.9009 |
| 1 NAM vs 2 NAMs | 0.1722 | 3.827 | P < 0.05 | 0.01667 to 0.3277 |
| 1 NAM vs 3 NAMs | 0.1256 | 1.549 | P > 0.05 | −0.1546 to 0.4059 |
| 1 NAM vs K65R | 0.1565 | 1.856 | P > 0.05 | −0.1349 to 0.4480 |
| 1 NAM vs M184V | 0.001657 | 0.09786 | P > 0.05 | −0.05687 to 0.06018 |
| 1 NAM vs T69 | −0.09534 | 1.905 | P > 0.05 | −0.2683 to 0.07766 |
| 1 NAM vs K65R + M184V | 0.2694 | 4.564 | P < 0.001 | 0.06538 to 0.4734 |

TABLE 2-continued

Bonferroni's Multiple Comparison Test - EFV Hypersusceptibility

| Values Compared | Mean Diff. | t | P value | 95% CI of diff |
|---|---|---|---|---|
| 1 NAM vs T215Y_3_TAMs | 0.2651 | 4.633 | P < 0.001 | 0.06734 to 0.4629 |
| 1 NAM vs T215Y_3_TAMs_208 | 0.3294 | 2.174 | P > 0.05 | −0.1943 to 0.8532 |
| 1 NAM vs T215Y_3_TAMs_no208 | 0.2549 | 4.148 | P < 0.01 | 0.04252 to 0.4673 |
| 1 NAM vs K70R_3_TAMs | −0.02778 | 0.4969 | P > 0.05 | −0.2210 to 0.1655 |
| 1 NAM vs T215Y_3_TAMs_no118 | 0.2225 | 3.037 | P > 0.05 | −0.03071 to 0.4757 |
| 1 NAM vs T215Y_3_TAMs_118 | 0.3291 | 3.683 | P < 0.05 | 0.02025 to 0.6379 |
| 2 NAMs vs 3 NAMs | −0.04654 | 0.51 | P > 0.05 | −0.3619 to 0.2689 |
| 2 NAMs vs K65R | −0.01562 | 0.1659 | P > 0.05 | −0.3410 to 0.3098 |
| 2 NAMs vs M184V | −0.1705 | 3.776 | P < 0.05 | −0.3266 to −0.01444 |
| 2 NAMs vs T69 | −0.2675 | 4.1 | P < 0.01 | −0.4930 to −0.04199 |
| 2 NAMs vs K65R + M184V | 0.09723 | 1.344 | P > 0.05 | −0.1529 to 0.3473 |
| 2 NAMs vs T215Y_3_TAMs | 0.09297 | 1.311 | P > 0.05 | −0.1521 to 0.3380 |
| 2 NAMs vs T215Y_3_TAMs_208 | 0.1573 | 1 | P > 0.05 | −0.3861 to 0.7007 |
| 2 NAMs vs T215Y_3_TAMs_no208 | 0.08272 | 1.113 | P > 0.05 | −0.1743 to 0.3397 |
| 2 NAMs vs K70R_3_TAMs | −0.1999 | 2.863 | P > 0.05 | −0.4413 to 0.04144 |
| 2 NAMs vs T215Y_3_TAMs_no118 | 0.05035 | 0.5967 | P > 0.05 | −0.2413 to 0.3420 |
| 2 NAMs vs T215Y_3_TAMs_118 | 0.1569 | 1.59 | P > 0.05 | −0.1841 to 0.4979 |
| 3 NAMs vs K65R | 0.03092 | 0.2669 | P > 0.05 | −0.3694 to 0.4312 |
| 3 NAMs vs M184V | −0.124 | 1.527 | P > 0.05 | −0.4045 to 0.1566 |
| 3 NAMs vs T69 | −0.221 | 2.354 | P > 0.05 | −0.5453 to 0.1034 |
| 3 NAMs vs K65R + M184V | 0.1438 | 1.453 | P > 0.05 | −0.1982 to 0.4857 |
| 3 NAMs vs T215Y_3_TAMs | 0.1395 | 1.425 | P > 0.05 | −0.1988 to 0.4778 |
| 3 NAMs vs T215Y_3_TAMs_208 | 0.2038 | 1.191 | P > 0.05 | −0.3875 to 0.7951 |
| 3 NAMs vs T215Y_3_TAMs_no208 | 0.1293 | 1.288 | P > 0.05 | −0.2177 to 0.4763 |
| 3 NAMs vs K70R_3_TAMs | −0.1534 | 1.58 | P > 0.05 | −0.4890 to 0.1822 |
| 3 NAMs vs T215Y_3_TAMs_no118 | 0.09689 | 0.8968 | P > 0.05 | −0.2765 to 0.4703 |
| 3 NAMs vs T215Y_3_TAMs_118 | 0.2035 | 1.702 | P > 0.05 | −0.2097 to 0.6166 |
| K65R vs M184V | −0.1549 | 1.835 | P > 0.05 | −0.4467 to 0.1369 |
| K65R vs T69 | −0.2519 | 2.606 | P > 0.05 | −0.5860 to 0.08224 |
| K65R vs K65R + M184V | 0.1129 | 1.111 | P > 0.05 | −0.2383 to 0.4640 |
| K65R vs T215Y_3_TAMs | 0.1086 | 1.08 | P > 0.05 | −0.2390 to 0.4562 |
| K65R vs T215Y_3_TAMs_208 | 0.1729 | 1.001 | P > 0.05 | −0.4238 to 0.7696 |
| K65R vs T215Y_3_TAMs_no208 | 0.09835 | 0.9545 | P > 0.05 | −0.2578 to 0.4545 |
| K65R vs K70R_3_TAMs | −0.1843 | 1.846 | P > 0.05 | −0.5294 to 0.1607 |
| K65R vs T215Y_3_TAMs_no118 | 0.06597 | 0.5971 | P > 0.05 | −0.3159 to 0.4479 |
| K65R vs T215Y_3_TAMs_118 | 0.1725 | 1.417 | P > 0.05 | −0.2483 to 0.5933 |
| M184V vs T69 | −0.09699 | 1.932 | P > 0.05 | −0.2705 to 0.07651 |
| M184V vs K65R + M184V | 0.2677 | 4.526 | P < 0.001 | 0.06329 to 0.4722 |
| M184V vs T215Y_3_TAMs | 0.2635 | 4.594 | P < 0.001 | 0.06524 to 0.4617 |
| M184V vs T215Y_3_TAMs_208 | 0.3278 | 2.162 | P > 0.05 | −0.1962 to 0.8517 |
| M184V vs T215Y_3_TAMs_no208 | 0.2532 | 4.113 | P < 0.01 | 0.04044 to 0.4660 |
| M184V vs K70R_3_TAMs | −0.02944 | 0.5253 | P > 0.05 | −0.2231 to 0.1643 |
| M184V vs T215Y_3_TAMs_no118 | 0.2209 | 3.01 | P > 0.05 | −0.03272 to 0.4744 |
| M184V vs T215Y_3_TAMs_118 | 0.3274 | 3.661 | P < 0.05 | 0.01831 to 0.6365 |
| T69 vs K65R + M184V | 0.3647 | 4.823 | P < 0.001 | 0.1034 to 0.6261 |
| T69 vs T215Y_3_TAMs | 0.3605 | 4.857 | P < 0.001 | 0.1040 to 0.6170 |
| T69 vs T215Y_3_TAMs_208 | 0.4248 | 2.676 | P > 0.05 | −0.1239 to 0.9734 |
| T69 vs T215Y_3_TAMs_no208 | 0.3502 | 4.518 | P < 0.001 | 0.08231 to 0.6181 |
| T69 vs K70R_3_TAMs | 0.06756 | 0.9228 | P > 0.05 | −0.1855 to 0.3206 |
| T69 vs T215Y_3_TAMs_no118 | 0.3179 | 3.646 | P < 0.05 | 0.01652 to 0.6192 |
| T69 vs T215Y_3_TAMs_118 | 0.4244 | 4.199 | P < 0.01 | 0.07506 to 0.7738 |
| K65R + M184V vs T215Y_3_TAMs | −0.004258 | 0.05287 | P > 0.05 | −0.2826 to 0.2741 |
| K65R + M184V vs T215Y_3_TAMs_208 | 0.06005 | 0.3711 | P > 0.05 | −0.4992 to 0.6193 |
| K65R + M184V vs T215Y_3_TAMs_no208 | −0.01451 | 0.1736 | P > 0.05 | −0.3034 to 0.2744 |
| K65R + M184V vs K70R_3_TAMs | −0.2972 | 3.733 | P < 0.05 | −0.5723 to −0.02202 |
| K65R + M184V vs T215Y_3_TAMs_no118 | −0.04688 | 0.5061 | P > 0.05 | −0.3670 to 0.2733 |
| K65R + M184V vs T215Y_3_TAMs_118 | 0.05968 | 0.564 | P > 0.05 | −0.3060 to 0.4254 |
| T215Y_3_TAMs vs T215Y_3_TAMs_208 | 0.06431 | 0.399 | P > 0.05 | −0.4927 to 0.6213 |
| T215Y_3_TAMs vs T215Y_3_TAMs_no208 | −0.01025 | 0.1245 | P > 0.05 | −0.2948 to 0.2743 |
| T215Y_3_TAMs vs K70R_3_TAMs | −0.2929 | 3.742 | P < 0.05 | −0.5635 to −0.02234 |
| T215Y_3_TAMs vs T215Y_3_TAMs_no118 | −0.04263 | 0.4659 | P > 0.05 | −0.3589 to 0.2736 |
| T215Y_3_TAMs vs T215Y_3_TAMs_118 | 0.06394 | 0.61 | P > 0.05 | −0.2983 to 0.4262 |
| T215Y_3_TAMs_208 vs T215Y_3_TAMs_no208 | −0.07456 | 0.4583 | P > 0.05 | −0.6369 to 0.4878 |
| T215Y_3_TAMs_208 vs K70R_3_TAMs | −0.3572 | 2.223 | P > 0.05 | −0.9126 to 0.1981 |
| T215Y_3_TAMs_208 vs T215Y_3_TAMs_no118 | −0.1069 | 0.6383 | P > 0.05 | −0.6859 to 0.4721 |
| T215Y_3_TAMs_208 vs T215Y_3_TAMs_118 | −0.0003693 | 0.002108 | P > 0.05 | −0.6057 to 0.6050 |
| T215Y_3_TAMs_no208 vs K70R_3_TAMs | −0.2827 | 3.472 | P < 0.05 | −0.5641 to −0.001258 |
| T215Y_3_TAMs_no208 vs T215Y_3_TAMs_no118 | −0.03237 | 0.3437 | P > 0.05 | −0.3579 to 0.2932 |
| T215Y_3_TAMs_no208 vs T215Y_3_TAMs_118 | 0.07419 | 0.6922 | P > 0.05 | −0.2963 to 0.4446 |
| K70R_3_TAMs vs T215Y_3_TAMs_no118 | 0.2503 | 2.76 | P > 0.05 | −0.06310 to 0.5637 |
| K70R_3_TAMs vs T215Y_3_TAMs_118 | 0.3569 | 3.428 | P > 0.05 | −0.002953 to 0.7167 |
| T215Y_3_TAMs_no118 vs T215Y_3_TAMs_118 | 0.1066 | 0.9317 | P > 0.05 | −0.2887 to 0.5018 |

TABLE 3

| Bonferroni's Multiple Comparison Test - NVP Hypersusceptibility | | | | |
|---|---|---|---|---|
| Values Compares | Mean Diff. | t | P value | 95% CI of diff |
| wt vs 1 NAM | 0.1982 | 7.291 | P < 0.001 | 0.1043 to 0.2922 |
| wt vs 2 NAMs | 0.4677 | 4.995 | P < 0.001 | 0.1441 to 0.7913 |
| wt vs 3 NAMs | 0.4192 | 2.436 | P > 0.05 | −0.1756 to 1.014 |
| wt vs K65R | 0.5344 | 2.983 | P > 0.05 | −0.08467 to 1.153 |
| wt vs M184V | 0.1847 | 6.499 | P < 0.001 | 0.08646 to 0.2829 |
| wt vs T69 | 0.1598 | 1.526 | P > 0.05 | −0.2022 to 0.5218 |
| wt vs K65R + M184V | 0.5769 | 4.64 | P < 0.001 | 0.1472 to 1.007 |
| wt vs T215Y_3_TAMs | 0.4092 | 3.399 | P > 0.05 | −0.006911 to 0.8254 |
| wt vs T215Y_3_TAMs_208 | 0.4535 | 1.401 | P > 0.05 | −0.6650 to 1.572 |
| wt vs T215Y_3_TAMs_no208 | 0.4022 | 3.104 | P > 0.05 | −0.04567 to 0.8500 |
| wt vs K70R_3_TAMs | 0.2866 | 2.438 | P > 0.05 | −0.1196 to 0.6928 |
| wt vs T215Y_3_TAMs_no118 | 0.4157 | 2.679 | P > 0.05 | −0.1207 to 0.9521 |
| wt vs T215Y_3_TAMs_118 | 0.3995 | 2.103 | P > 0.05 | −0.2569 to 1.056 |
| 1 NAM vs 2 NAMs | 0.2694 | 2.797 | P > 0.05 | −0.06346 to 0.6023 |
| 1 NAM vs 3 NAMs | 0.221 | 1.273 | P > 0.05 | −0.3790 to 0.8209 |
| 1 NAM vs K65R | 0.3361 | 1.862 | P > 0.05 | −0.2878 to 0.9601 |
| 1 NAM vs M184V | −0.01357 | 0.3737 | P > 0.05 | −0.1391 to 0.1119 |
| 1 NAM vs T69 | −0.03843 | 0.3586 | P > 0.05 | −0.4088 to 0.3319 |
| 1 NAM vs K65R + M184V | 0.3786 | 2.996 | P > 0.05 | −0.05809 to 0.8154 |
| 1 NAM vs T215Y_3_TAMs | 0.211 | 1.722 | P > 0.05 | −0.2124 to 0.6344 |
| 1 NAM vs T215Y_3_TAMs_208 | 0.2552 | 0.7868 | P > 0.05 | −0.8660 to 1.376 |
| 1 NAM vs T215Y_3_TAMs_no208 | 0.204 | 1.551 | P > 0.05 | −0.2507 to 0.6586 |
| 1 NAM vs K70R_3_TAMs | 0.08835 | 0.7382 | P > 0.05 | −0.3253 to 0.5020 |
| 1 NAM vs T215Y_3_TAMs_no118 | 0.2175 | 1.387 | P > 0.05 | −0.3246 to 0.7596 |
| 1 NAM vs T215Y_3_TAMs_118 | 0.2013 | 1.052 | P > 0.05 | −0.4598 to 0.8623 |
| 2 NAMs vs 3 NAMs | −0.04846 | 0.2481 | P > 0.05 | −0.7236 to 0.6267 |
| 2 NAMs vs K65R | 0.06669 | 0.3309 | P > 0.05 | −0.6299 to 0.7632 |
| 2 NAMs vs M184V | −0.283 | 2.927 | P > 0.05 | −0.6171 to 0.05111 |
| 2 NAMs vs T69 | −0.3079 | 2.204 | P > 0.05 | −0.7906 to 0.1749 |
| 2 NAMs vs K65R + M184V | 0.1092 | 0.7051 | P > 0.05 | −0.4262 to 0.6446 |
| 2 NAMs vs T215Y_3_TAMs | −0.05842 | 0.3849 | P > 0.05 | −0.5830 to 0.4662 |
| 2 NAMs vs T215Y_3_TAMs_208 | −0.01419 | 0.04216 | P > 0.05 | −1.177 to 1.149 |
| 2 NAMs vs T215Y_3_TAMs_no208 | −0.06547 | 0.4114 | P > 0.05 | −0.6155 to 0.4846 |
| 2 NAMs vs K70R_3_TAMs | −0.1811 | 1.211 | P > 0.05 | −0.6978 to 0.3356 |
| 2 NAMs vs T215Y_3_TAMs_no118 | −0.05192 | 0.2874 | P > 0.05 | −0.6762 to 0.5724 |
| 2 NAMs vs T215Y_3_TAMs_118 | −0.06817 | 0.3227 | P > 0.05 | −0.7982 to 0.6618 |
| 3 NAMs vs K65R | 0.1151 | 0.4644 | P > 0.05 | −0.7418 to 0.9721 |
| 3 NAMs vs M184V | −0.2345 | 1.35 | P > 0.05 | −0.8352 to 0.3661 |
| 3 NAMs vs T69 | −0.2594 | 1.291 | P > 0.05 | −0.9538 to 0.4350 |
| 3 NAMs vs K65R + M184V | 0.1577 | 0.7445 | P > 0.05 | −0.5743 to 0.8896 |
| 3 NAMs vs T215Y_3_TAMs | −0.009962 | 0.04755 | P > 0.05 | −0.7340 to 0.7141 |
| 3 NAMs vs T215Y_3_TAMs_208 | 0.03427 | 0.09357 | P > 0.05 | −1.231 to 1.300 |
| 3 NAMs vs T215Y_3_TAMs_no208 | −0.01701 | 0.07916 | P > 0.05 | −0.7598 to 0.7257 |
| 3 NAMs vs K70R_3_TAMs | −0.1326 | 0.6381 | P > 0.05 | −0.8510 to 0.5858 |
| 3 NAMs vs T215Y_3_TAMs_no118 | −0.003462 | 0.01497 | P > 0.05 | −0.8027 to 0.7958 |
| 3 NAMs vs T215Y_3_TAMs_118 | −0.01971 | 0.07704 | P > 0.05 | −0.9040 to 0.8646 |
| K65R vs M184V | −0.3497 | 1.935 | P > 0.05 | −0.9743 to 0.2749 |
| K65R vs T69 | −0.3746 | 1.81 | P > 0.05 | −1.090 to 0.3406 |
| K65R vs K65R + M184V | 0.04252 | 0.1955 | P > 0.05 | −0.7092 to 0.7943 |
| K65R vs T215Y_3_TAMs | −0.1251 | 0.5811 | P > 0.05 | −0.8692 to 0.6190 |
| K65R vs T215Y_3_TAMs_208 | −0.08088 | 0.2189 | P > 0.05 | −1.358 to 1.196 |
| K65R vs T215Y_3_TAMs_no208 | −0.1322 | 0.5992 | P > 0.05 | −0.8944 to 0.6301 |
| K65R vs K70R_3_TAMs | −0.2478 | 1.16 | P > 0.05 | −0.9863 to 0.4908 |
| K65R vs T215Y_3_TAMs_no118 | −0.1186 | 0.5015 | P > 0.05 | −0.9360 to 0.6988 |
| K65R vs T215Y_3_TAMs_118 | −0.1349 | 0.5175 | P > 0.05 | −1.036 to 0.7659 |
| M184V vs T69 | −0.02486 | 0.2313 | P > 0.05 | −0.3963 to 0.3466 |
| M184V vs K65R + M184V | 0.3922 | 3.097 | P > 0.05 | −0.04545 to 0.8299 |
| M184V vs T215Y_3_TAMs | 0.2246 | 1.829 | P > 0.05 | −0.1998 to 0.6490 |
| M184V vs T215Y_3_TAMs_208 | 0.2688 | 0.8284 | P > 0.05 | −0.8527 to 1.390 |
| M184V vs T215Y_3_TAMs_no208 | 0.2175 | 1.651 | P > 0.05 | −0.2380 to 0.6730 |
| M184V vs K70R_3_TAMs | 0.1019 | 0.8495 | P > 0.05 | −0.3127 to 0.5166 |
| M184V vs T215Y_3_TAMs_no118 | 0.2311 | 1.471 | P > 0.05 | −0.3117 to 0.7739 |
| M184V vs T215Y_3_TAMs_118 | 0.2148 | 1.122 | P > 0.05 | −0.4469 to 0.8765 |
| T69 vs K65R + M184V | 0.4171 | 2.577 | P > 0.05 | −0.1423 to 0.9765 |
| T69 vs T215Y_3_TAMs | 0.2494 | 1.57 | P > 0.05 | −0.2996 to 0.7985 |
| T69 vs T215Y_3_TAMs_208 | 0.2937 | 0.8642 | P > 0.05 | −0.8808 to 1.468 |
| T69 vs T215Y_3_TAMs_no208 | 0.2424 | 1.461 | P > 0.05 | −0.3311 to 0.8159 |
| T69 vs K70R_3_TAMs | 0.1268 | 0.809 | P > 0.05 | −0.4148 to 0.6684 |
| T69 vs T215Y_3_TAMs_no118 | 0.2559 | 1.371 | P > 0.05 | −0.3891 to 0.9010 |
| T69 vs T215Y_3_TAMs_118 | 0.2397 | 1.108 | P > 0.05 | −0.5081 to 0.9875 |
| K65R + M184V vs T215Y_3_TAMs | −0.1676 | 0.9723 | P > 0.05 | −0.7635 to 0.4283 |
| K65R + M184V vs T215Y_3_TAMs_208 | −0.1234 | 0.3563 | P > 0.05 | −1.320 to 1.074 |
| K65R + M184V vs T215Y_3_TAMs_no208 | −0.1747 | 0.9762 | P > 0.05 | −0.7931 to 0.4438 |
| K65R + M184V vs K70R_3_TAMs | −0.2903 | 1.703 | P > 0.05 | −0.8793 to 0.2987 |
| K65R + M184V vs T215Y_3_TAMs_no118 | −0.1611 | 0.8126 | P > 0.05 | −0.8464 to 0.5242 |
| K65R + M184V vs T215Y_3_TAMs_118 | −0.1774 | 0.7831 | P > 0.05 | −0.9602 to 0.6055 |

TABLE 3-continued

Bonferroni's Multiple Comparison Test - NVP Hypersusceptibility

| Values Compares | Mean Diff. | t | P value | 95% CI of diff |
|---|---|---|---|---|
| T215Y_3_TAMs vs T215Y_3_TAMs_208 | 0.04423 | 0.1282 | P > 0.05 | −1.148 to 1.236 |
| T215Y_3_TAMs vs T215Y_3_TAMs_no208 | −0.007051 | 0.04001 | P > 0.05 | −0.6162 to 0.6021 |
| T215Y_3_TAMs vs K70R_3_TAMs | −0.1227 | 0.732 | P > 0.05 | −0.7019 to 0.4565 |
| T215Y_3_TAMs vs T215Y_3_TAMs_no118 | 0.0065 | 0.03319 | P > 0.05 | −0.6704 to 0.6834 |
| T215Y_3_TAMs vs T215Y_3_TAMs_118 | −0.00975 | 0.04345 | P > 0.05 | −0.7852 to 0.7657 |
| T215Y_3_TAMs_208 vs T215Y_3_TAMs_no208 | −0.05128 | 0.1472 | P > 0.05 | −1.255 to 1.152 |
| T215Y_3_TAMs_208 vs K70R_3_TAMs | −0.1669 | 0.4852 | P > 0.05 | −1.356 to 1.022 |
| T215Y_3_TAMs_208 vs T215Y_3_TAMs_no118 | −0.03773 | 0.1052 | P > 0.05 | −1.277 to 1.202 |
| T215Y_3_TAMs_208 vs T215Y_3_TAMs_118 | −0.05398 | 0.144 | P > 0.05 | −1.350 to 1.242 |
| T215Y_3_TAMs_no208 vs K70R_3_TAMs | −0.1156 | 0.6634 | P > 0.05 | −0.7180 to 0.4868 |
| T215Y_3_TAMs_no208 vs T215Y_3_TAMs_no118 | 0.01355 | 0.06721 | P > 0.05 | −0.6833 to 0.7104 |
| T215Y_3_TAMs_no208 vs T215Y_3_TAMs_118 | −0.002699 | 0.01177 | P > 0.05 | −0.7956 to 0.7902 |
| K70R_3_TAMs vs T215Y_3_TAMs_no118 | 0.1292 | 0.6655 | P > 0.05 | −0.5417 to 0.8000 |
| K70R_3_TAMs vs T215Y_3_TAMs_118 | 0.1129 | 0.5067 | P > 0.05 | −0.6573 to 0.8831 |
| T215Y_3_TAMs_no118 vs T215Y_3_TAMs_118 | −0.01625 | 0.06638 | P > 0.05 | −0.8624 to 0.8299 |

TABLE 4

Bonferroni's Multiple Comparison Test - DLV

| Values Compared | Mean Diff. | t | P value | 95% CI of diff |
|---|---|---|---|---|
| wt vs 1 NAM | 0.3819 | 11.36 | P < 0.001 | 0.2656 to 0.4981 |
| wt vs 2 NAMs | 0.6804 | 5.945 | P < 0.001 | 0.2848 to 1.076 |
| wt vs 3 NAMs | 0.6749 | 3.208 | P > 0.05 | −0.05225 to 1.402 |
| wt vs K65R | 0.7687 | 3.511 | P < 0.05 | 0.01193 to 1.525 |
| wt vs M184V | 0.3741 | 10.63 | P < 0.001 | 0.2525 to 0.4957 |
| wt vs T69 | 0.2562 | 2.001 | P > 0.05 | −0.1863 to 0.6988 |
| wt vs K65R + M184V | 0.8932 | 5.877 | P < 0.001 | 0.3679 to 1.419 |
| wt vs T215Y_3_TAMs | 1.06 | 7.113 | P < 0.001 | 0.5451 to 1.575 |
| wt vs T215Y_3_TAMs_208 | 1.165 | 2.945 | P > 0.05 | −0.2024 to 2.532 |
| wt vs T215Y_3_TAMs_no208 | 1.043 | 6.489 | P < 0.001 | 0.4876 to 1.599 |
| wt vs K70R_3_TAMs | −0.1936 | 1.34 | P > 0.05 | −0.6932 to 0.3059 |
| wt vs T215Y_3_TAMs_no118 | 1.08 | 5.634 | P < 0.001 | 0.4175 to 1.743 |
| wt vs T215Y_3_TAMs_118 | 1.03 | 4.367 | P < 0.01 | 0.2149 to 1.845 |
| 1 NAM vs 2 NAMs | 0.2985 | 2.533 | P > 0.05 | −0.1088 to 0.7059 |
| 1 NAM vs 3 NAMs | 0.293 | 1.381 | P > 0.05 | −0.4406 to 1.027 |
| 1 NAM vs K65R | 0.3868 | 1.752 | P > 0.05 | −0.3761 to 1.150 |
| 1 NAM vs M184V | −0.007762 | 0.1724 | P > 0.05 | −0.1634 to 0.1478 |
| 1 NAM vs T69 | −0.1256 | 0.9585 | P > 0.05 | −0.5787 to 0.3274 |
| 1 NAM vs K65R + M184V | 0.5114 | 3.309 | P > 0.05 | −0.02281 to 1.046 |
| 1 NAM vs T215Y_3_TAMs | 0.6784 | 4.473 | P < 0.001 | 0.1542 to 1.203 |
| 1 NAM vs T215Y_3_TAMs_208 | 0.7831 | 1.974 | P > 0.05 | −0.5877 to 2.154 |
| 1 NAM vs T215Y_3_TAMs_no208 | 0.6612 | 4.052 | P < 0.01 | 0.09727 to 1.225 |
| 1 NAM vs K70R_3_TAMs | −0.5755 | 3.909 | P < 0.01 | −1.084 to −0.06663 |
| 1 NAM vs T215Y_3_TAMs_no118 | 0.6983 | 3.604 | P < 0.05 | 0.02854 to 1.368 |
| 1 NAM vs T215Y_3_TAMs_118 | 0.6483 | 2.729 | P > 0.05 | −0.1727 to 1.469 |
| 2 NAMs vs 3 NAMs | −0.005498 | 0.02303 | P > 0.05 | −0.8308 to 0.8198 |
| 2 NAMs vs KG5R | 0.08826 | 0.3583 | P > 0.05 | −0.7632 to 0.9398 |
| 2 NAMS vs M184V | −0.3063 | 2.589 | P > 0.05 | −0.7152 to 0.1026 |
| 2 NAMs vs T69 | −0.4242 | 2.484 | P > 0.05 | −1.014 to 0.1659 |
| 2 NAMs vs K65R + M184V | 0.2128 | 1.124 | P > 0.05 | −0.4416 to 0.8673 |
| 2 NAMs vs T215Y_3_TAMs | 0.3799 | 2.031 | P > 0.05 | −0.2665 to 1.026 |
| 2 NAMs vs T215Y_3_TAMs_208 | 0.4845 | 1.178 | P > 0.05 | −0.9374 to 1.906 |
| 2 NAMs vs T215Y_3_TAMs_no208 | 0.3627 | 1.846 | P > 0.05 | −0.3163 to 1.042 |
| 2 NAMs vs K70R_3_TAMs | −0.874 | 4.765 | P < 0.001 | −1.508 to −0.2401 |
| 2 NAMs vs T215Y_3_TAMs_no118 | 0.3997 | 1.796 | P > 0.05 | −0.3694 to 1.169 |
| 2 NAMs vs T215Y_3_TAMs_118 | 0.3498 | 1.337 | P > 0.05 | −0.5541 to 1.254 |
| 3 NAMs vs K65R | 0.09376 | 0.3094 | P > 0.05 | −0.9538 to 1.141 |
| 3 NAMs vs M184V | −0.3008 | 1.415 | P > 0.05 | −1.035 to 0.4337 |
| 3 NAMs vs T69 | −0.4187 | 1.705 | P > 0.05 | −1.268 to 0.4301 |
| 3 NAMs vs K65R + M184V | 0.2183 | 0.8434 | P > 0.05 | −0.6764 to 1.113 |
| 3 NAMs vs T215Y_3_TAMs | 0.3854 | 1.499 | P > 0.05 | −0.5035 to 1.274 |
| 3 NAMs vs T215Y_3_TAMs_208 | 0.49 | 1.095 | P > 0.05 | −1.057 to 2.037 |
| 3 NAMs vs T215Y_3_TAMs_no208 | 0.3682 | 1.394 | P > 0.05 | −0.5447 to 1.281 |
| 3 NAMs vs K70R_3_TAMs | −0.8685 | 3.412 | P > 0.05 | −1.748 to 0.01135 |
| 3 NAMs vs T215Y_3_TAMs_no118 | 0.4052 | 1.427 | P > 0.05 | −0.5765 to 1.387 |
| 3 NAMs vs T215Y_3_TAMs_118 | 0.3553 | 1.126 | P > 0.05 | −0.7353 to 1.446 |
| K65R vs M184V | −0.3946 | 1.785 | P > 0.05 | −1.158 to 0.3692 |
| K65R vs T69 | −0.5124 | 2.026 | P > 0.05 | −1.387 to 0.3619 |
| K65R vs K65R + M184V | 0.1246 | 0.4685 | P > 0.05 | −0.7944 to 1.044 |
| K65R vs T215Y_3_TAMs | 0.2916 | 1.104 | P > 0.05 | −0.6216 to 1.205 |
| K65R vs T215Y_3_TAMs_208 | 0.3963 | 0.8771 | P > 0.05 | −1.165 to 1.958 |

TABLE 4-continued

Bonferroni's Multiple Comparison Test - DLV

| Values Compared | Mean Diff. | t | P value | 95% CI of diff |
|---|---|---|---|---|
| K65R vs T215Y_3_TAMs_no208 | 0.2744 | 1.013 | P > 0.05 | −0.6621 to 1.211 |
| K65R vs K70R_3_TAMs | −0.9623 | 3.677 | P < 0.05 | −1.867 to −0.05782 |
| K65R vs T215Y_3_TAMs_no118 | 0.3115 | 1.072 | P > 0.05 | −0.6924 to 1.315 |
| K65R vs T215Y_3_TAMs_118 | 0.2615 | 0.814 | P > 0.05 | −0.8490 to 1.372 |
| M184V vs T69 | −0.1179 | 0.8965 | P > 0.05 | −0.5724 to 0.3366 |
| M184V vs K65R + M184V | 0.5191 | 3.351 | P > 0.05 | −0.01625 to 1.055 |
| M184V vs T215Y_3_TAMs | 0.6862 | 4.513 | P < 0.001 | 0.1607 to 1.212 |
| M184V vs T215Y_3_TAMs_208 | 0.7908 | 1.993 | P > 0.05 | −0.5804 to 2.162 |
| M184V vs T215Y_3_TAMs_no208 | 0.669 | 4.092 | P < 0.01 | 0.1039 to 1.234 |
| M184V vs K70R_3_TAMs | −0.5677 | 3.846 | P < 0.05 | −1.078 to −0.05761 |
| M184V vs T215Y_3_TAMs_no118 | 0.706 | 3.638 | P < 0.05 | 0.03534 to 1.377 |
| M184V vs T215Y_3_TAMs_118 | 0.6561 | 2.759 | P > 0.05 | −0.1657 to 1.478 |
| T69 vs K65R + M184V | 0.637 | 3.219 | P > 0.05 | −0.04685 to 1.321 |
| T69 vs T215Y_3_TAMs | 0.8041 | 4.11 | P < 0.01 | 0.1279 to 1.480 |
| T69 vs T215Y_3_TAMs_208 | 0.9087 | 2.188 | P > 0.05 | −0.5270 to 2.344 |
| T69 vs T215Y_3_TAMs_no208 | 0.7869 | 3.845 | P < 0.05 | 0.07951 to 1.494 |
| T69 vs K70R_3_TAMs | −0.4499 | 2.341 | P > 0.05 | −1.114 to 0.2144 |
| T69 vs T215Y_3_TAMs_no118 | 0.8239 | 3.585 | P < 0.05 | 0.02965 to 1.618 |
| T69 vs T215Y_3_TAMs_118 | 0.774 | 2.891 | P > 0.05 | −0.1514 to 1.699 |
| K65R + M184V vs T215Y_3_TAMs | 0.167 | 0.7877 | P > 0.05 | −0.5659 to 0.9000 |
| K65R + M184V vs T215Y_3_TAMs_208 | 0.2717 | 0.6417 | P > 0.05 | −1.192 to 1.735 |
| K65R + M184V vs T215Y_3_TAMs_no208 | 0.1499 | 0.6798 | P > 0.05 | −0.6120 to 0.9118 |
| K65R + M184V vs K70R_3_TAMs | −1.087 | 5.202 | P < 0.001 | −1.809 to −0.3648 |
| K65R + M184V vs T215Y_3_TAMs_no118 | 0.1869 | 0.7661 | P > 0.05 | −0.6563 to 1.030 |
| K65R + M184V vs T215Y_3_TAMs_118 | 0.137 | 0.4892 | P > 0.05 | −0.8308 to 1.105 |
| T215Y_3_TAMs vs T215Y_3_TAMs_208 | 0.1046 | 0.2478 | P > 0.05 | −1.355 to 1.564 |
| T215Y_3_TAMs vs T215Y_3_TAMs_no208 | −0.01718 | 0.07865 | P > 0.05 | −0.7721 to 0.7378 |
| T215Y_3_TAMs vs K70R_3_TAMs | −1.254 | 6.064 | P < 0.001 | −1.969 to −0.5392 |
| T215Y_3_TAMs vs T215Y_3_TAMs_no118 | 0.01984 | 0.08194 | P > 0.05 | −0.8171 to 0.8567 |
| T215Y_3_TAMs vs T215Y_3_TAMs_118 | −0.03008 | 0.108 | P > 0.05 | −0.9924 to 0.9322 |
| T215Y_3_TAMs_208 vs T215Y_3_TAMs_no208 | −0.1218 | 0.2855 | P > 0.05 | −1.596 to 1.353 |
| T215Y_3_TAMs_208 vs K70R_3_TAMs | −1.359 | 3.229 | P > 0.05 | −2.813 to 0.09571 |
| T215Y_3_TAMs_208 vs T215Y_3_TAMs_no118 | −0.0848 | 0.1931 | P > 0.05 | −1.603 to 1.433 |
| T215Y_3_TAMs_208 vs T215Y_3_TAMs_118 | −0.1347 | 0.2927 | P > 0.05 | −1.725 to 1.456 |
| T215Y_3_TAMs_no208 vs K70R_3_TAMs | −1.237 | 5.742 | P < 0.001 | −1.981 to −0.4924 |
| T215Y_3_TAMs_no208 vs T215Y_3_TAMs_no118 | 0.03702 | 0.1484 | P > 0.05 | −0.8253 to 0.8994 |
| T215Y_3_TAMs_no208 vs T215Y_3_TAMs_118 | −0.0129 | 0.0453 | P > 0.05 | −0.9974 to 0.9716 |
| K70R_3_TAMs vs T215Y_3_TAMs_no118 | 1.274 | 5.321 | P < 0.001 | 0.4464 to 2.101 |
| K70R_3_TAMs vs T215Y_3_TAMs_118 | 1.224 | 4.434 | P < 0.001 | 0.2698 to 2.178 |
| T215Y_3_TAMs_no118 vs T215Y_3_TAMs_118 | −0.04992 | 0.1645 | P > 0.05 | −1.099 to 0.9987 |

What is claimed is:

1. A method for treating a patient having a human immunodeficiency virus 1 (HIV-1) infection, comprising:
   (a) obtaining or having obtained a nucleic acid encoding reverse transcriptase of an HIV-1;
   (b) detecting or having detected in the nucleic acid the presence or absence of a mutation at codon 184 in combination with a mutation in codon 74, wherein the codon number of said HIV-1 corresponds to the codon number in the wild type HIV-1 isolate NL4-3, wherein the mutation at codon 184 encodes isoleucine (I) instead of methionine (M), and wherein the mutation at codon 74 encodes valine (V) instead of leucine (L);
   (c) determining or having determined that the HIV-1 is hypersusceptible to a non-nucleoside reverse transcriptase inhibitor (NNRTI) if the mutations are present; and
   (d) treating the patient with an effective amount of the NNRTI if the HIV-1 is determined to be hypersusceptible to the NNRTI in step (c).

2. The method of claim 1, further comprising in step b): detecting or having detected in the nucleic acid the presence or absence of a mutation in at least one of codon 210 or 219, wherein the mutation at codon 210 encodes tryptophan (W) instead of leucine (L), and wherein the mutation at codon 219 encodes glutamic acid (E), histidine (H), asparagine (N), glutamine (Q), or arginine (R) instead of lysine (K).

3. The method of claim 1, wherein the NNRTI is efavirenz (EFV), nevirapine (NVP), or delavirdine (DLV).

4. The method of claim 1, wherein the NNRTI is EFV.

5. The method of claim 1, wherein the NNRTI is NVP.

6. The method of claim 1, wherein the NNRTI is DLV.

7. The method of claim 1, further comprising in step b): detecting or having detected in the nucleic acid the presence or absence of a mutation at codon 69, wherein the mutation at codon 69 encodes alanine (A), aspartic acid (D), asparagine (N), or serine (S), instead of threonine (T).

8. The method of claim 1, further comprising in step b): detecting or having detected in the nucleic acid the presence or absence of a mutation in at least one of codon 41, 67, 70, and 215, wherein the mutation at codon 41 encodes leucine (L) instead of methionine (M), the mutation at codon 67 encodes asparagine (N) instead of aspartic acid (D), the mutation at codon 70 encodes arginine (R) instead of lysine (K), and the mutation at codon 215 encodes tyrosine (Y) instead of threonine (T).

9. The method of claim 8, wherein a mutation at codon 41 is detected.

10. The method of claim 8, wherein a mutation at codon 67 is detected.

11. The method of claim 8, wherein a mutation at codon 70 is detected.

12. The method of claim 8, wherein a mutation at codon 215 is detected.

* * * * *

SEQUENCE LISTING

<160> NUMBER OF SEQ ID NOS: 4

<210> SEQ ID NO 1
<211> LENGTH: 560
<212> TYPE: PRT
<213> ORGANISM: Artificial Sequence
<220> FEATURE:
<223> OTHER INFORMATION: HIV-1 vector pNL4-3

<400> SEQUENCE: 1

```
Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Val Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95
```

```
Pro Ala Gly Leu Lys Gln Lys Ser Val Thr Val Leu Asp Val Gly
            100                 105                 110

Asp Ala Tyr Phe Ser Val Pro Leu Asp Lys Asp Phe Arg Lys Tyr Thr
            115                 120                 125

Ala Phe Thr Ile Pro Ser Ile Asn Asn Glu Thr Pro Gly Ile Arg Tyr
        130                 135                 140

Gln Tyr Asn Val Leu Pro Gln Gly Trp Lys Gly Ser Pro Ala Ile Phe
145                 150                 155                 160

Gln Cys Ser Met Thr Lys Ile Leu Glu Pro Phe Arg Lys Gln Asn Pro
                165                 170                 175

Asp Ile Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Gln His
        195                 200                 205

Leu Leu Arg Trp Gly Phe Thr Thr Pro Asp Lys Lys His Gln Lys Glu
210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Gln Lys Leu Val Gly Lys Leu Asn Trp Ala Ser Gln Ile Tyr Ala
            260                 265                 270

Gly Ile Lys Val Arg Gln Leu Cys Lys Leu Leu Arg Gly Thr Lys Ala
        275                 280                 285

Leu Thr Glu Val Val Pro Leu Thr Glu Glu Ala Glu Leu Glu Leu Ala
290                 295                 300

Glu Asn Arg Glu Ile Leu Lys Glu Pro Val His Gly Val Tyr Tyr Asp
305                 310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
            340                 345                 350

Lys Tyr Ala Arg Met Lys Gly Ala His Thr Asn Asp Val Lys Gln Leu
        355                 360                 365

Thr Glu Ala Val Gln Lys Ile Ala Thr Glu Ser Ile Val Ile Trp Gly
370                 375                 380

Lys Thr Pro Lys Phe Lys Leu Pro Ile Gln Lys Glu Thr Trp Glu Ala
385                 390                 395                 400

Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Glu
            420                 425                 430

Pro Ile Ile Gly Ala Glu Thr Phe Tyr Val Asp Gly Ala Ala Asn Arg
        435                 440                 445

Glu Thr Lys Leu Gly Lys Ala Gly Tyr Val Thr Asp Arg Gly Arg Gln
450                 455                 460

Lys Val Val Pro Leu Thr Asp Thr Thr Asn Gln Lys Thr Glu Leu Gln
465                 470                 475                 480

Ala Ile His Leu Ala Leu Gln Asp Ser Gly Leu Glu Val Asn Ile Val
                485                 490                 495

Thr Asp Ser Gln Tyr Ala Leu Gly Ile Ile Gln Ala Gln Pro Asp Lys
            500                 505                 510
```

```
Ser Glu Ser Glu Leu Val Ser Gln Ile Ile Glu Gln Leu Ile Lys Lys
        515                 520                 525

Glu Lys Val Tyr Leu Ala Trp Val Pro Ala His Lys Gly Ile Gly Gly
    530                 535                 540

Asn Glu Gln Val Asp Gly Leu Val Ser Ala Gly Ile Arg Lys Val Leu
545                 550                 555                 560

<210> SEQ ID NO 2
<211> LENGTH: 14825
<212> TYPE: DNA
<213> ORGANISM: Artificial Sequence
<220> FEATURE:
<223> OTHER INFORMATION: Human immunodeficiency virus type 1

<400> SEQUENCE: 2
```

| | | | | |
|---|---|---|---|---|
| tggaagggct | aatttggtcc | caaaaaagac | aagagatcct | tgatctgtgg | atctaccaca | 60 |
| cacaaggcta | cttccctgat | tggcagaact | acacaccagg | gccagggatc | agatatccac | 120 |
| tgacctttgg | atggtgcttc | aagttagtac | cagttgaacc | agagcaagta | gaagaggcca | 180 |
| atgaaggaga | gaacaacagc | ttgttacacc | ctatgagcca | gcatgggatg | gaggacccgg | 240 |
| agggagaagt | attagtgtgg | aagtttgaca | gcctcctagc | atttcgtcac | atggcccgag | 300 |
| agctgcatcc | ggagtactac | aaagactgct | gacatcgagc | tttctacaag | ggactttccg | 360 |
| ctggggactt | tccagggagg | tgtggcctgg | gcgggactgg | ggagtggcga | gccctcagat | 420 |
| gctacatata | agcagctgct | ttttgcctgt | actgggtctc | tctggttaga | ccagatctga | 480 |
| gcctgggagc | tctctggcta | actagggaac | ccactgctta | agcctcaata | aagcttgcct | 540 |
| tgagtgctca | aagtagtgtg | tgcccgtctg | ttgtgtgact | ctggtaacta | gagatccctc | 600 |
| agacccttt | agtcagtgtg | gaaaatctct | agcagtggcg | cccgaacagg | gacttgaaag | 660 |
| cgaaagtaaa | gccagaggag | atctctcgac | gcaggactcg | gcttgctgaa | gcgcgcacgg | 720 |
| caagaggcga | ggggcggcga | ctggtgagta | cgccaaaaat | tttgactagc | ggaggctaga | 780 |
| aggagagaga | tgggtgcgag | agcgtcggta | ttaagcgggg | gagaattaga | taaatgggaa | 840 |
| aaaattcggt | taaggccagg | gggaaagaaa | caatataaac | taaaacatat | agtatgggca | 900 |
| agcagggagc | tagaacgatt | cgcagttaat | cctggccttt | tagagacatc | agaaggctgt | 960 |
| agacaaatac | tgggacagct | acaaccatcc | cttcagacag | gatcagaaga | acttagatca | 1020 |
| ttatataata | caatagcagt | cctctattgt | gtgcatcaaa | ggatagatgt | aaaagacacc | 1080 |
| aaggaagcct | tagataagat | agaggaagag | caaaacaaaa | gtaagaaaaa | ggcacagcaa | 1140 |
| gcagcagctg | acacaggaaa | caacagccag | gtcagccaaa | attaccctat | agtgcagaac | 1200 |
| ctccaggggc | aaatggtaca | tcaggccata | tcacctagaa | ctttaaatgc | atgggtaaaa | 1260 |
| gtagtagaag | agaaggcttt | cagcccagaa | gtaataccca | tgttttcagc | attatcagaa | 1320 |
| ggagccaccc | cacaagattt | aaataccatg | ctaaacacag | tggggggaca | tcaagcagcc | 1380 |
| atgcaaatgt | taaaagagac | catcaatgag | gaagctgcag | aatgggatag | attgcatcca | 1440 |
| gtgcatgcag | ggcctattgc | accaggccag | atgagagaac | caaggggaag | tgacatagca | 1500 |
| ggaactacta | gtacccttca | ggaacaaata | ggatggatga | cacataatcc | acctatccca | 1560 |
| gtaggagaaa | tctataaaag | atggataatc | ctgggattaa | ataaaatagt | aagaatgtat | 1620 |
| agccctacca | gcattctgga | cataagacaa | ggaccaaagg | aaccctttag | agactatgta | 1680 |
| gaccgattct | ataaaactct | aagagccgag | caagcttcac | aagaggtaaa | aaattggatg | 1740 |
| acagaaacct | tgttggtcca | aaatgcgaac | ccagattgta | agactatttt | aaaagcattg | 1800 |

```
ggaccaggag cgacactaga agaaatgatg acagcatgtc agggagtggg gggacccggc   1860
cataaagcaa gagttttggc tgaagcaatg agccaagtaa caaatccagc taccataatg   1920
atacagaaag gcaattttag gaaccaaaga aagactgtta agtgtttcaa ttgtggcaaa   1980
gaagggcaca tagccaaaaa ttgcagggcc cctaggaaaa agggctgttg aaatgtggaa   2040
aaggaaggac accaaatgaa agattgtact gagagacagg ctaattttt  agggaagatc   2100 tggccttccc acaagggaag gccagggaat tttcttcaga gcagaccaga gccaacagcc   2160
ccaccagaag agagcttcag gtttggggaa gagacaacaa ctccctctca gaagcaggag   2220
ccgatagcaa aggaactgta tcctttagct tccctcagat cactctttgg cagcgacccc   2280
tcgtcacaat aaagataggg gggcaattaa aggaagctct attagataca ggagcagatg   2340
atacagtatt agaagaaatg aatttgccag gaagatggaa accaaaaatg ataggggaa    2400 ttggaggttt tatcaaagta agacagtatg atcagatact catagaaatc tgcggacata   2460
aagctatagg tacagtatta gtaggaccta cacctgtcaa cataattgga agaaatctgt   2520
tgactcagat tggctgcact ttaaattttc ccattagtcc tattgagact gtaccagtaa   2580
aattaaagcc aggaatggat ggcccaaaag ttaaacaatg gccattgaca gaagaaaaaa   2640
taaaagcatt agtagaaatt tgtacagaaa tggaaaagga aggaaaaatt tcaaaaattg   2700
ggcctgaaaa tccatacaat actccagtat ttgccataaa gaaaaaagac agtactaaat   2760
ggagaaaatt agtagatttc agagaactta ataagagaac tcaagatttc tgggaagttc   2820
aattaggaat accacatcct gcagggttaa acagaaaaaa atcagtaaca gtactggatg   2880
tgggcgatgc atatttttca gttcccttag ataaagactt caggaagtat actgcattta   2940
ccatacctag tataaacaat gagacaccag ggattagata tcagtacaat gtgcttccac   3000
agggatggaa aggatcacca gcaatattcc agtgtagcat gacaaaaatc ttagagcctt   3060
ttagaaaaca aaatccagac atagtcatct atcaatacat ggatgatttg tatgtaggat   3120
ctgacttaga aatagggcag catagaacaa aaatagagga actgagacaa catctgttga   3180
ggtggggatt taccacacca gacaaaaaac atcagaaaga acctccattc ctttggatgg   3240
gttatgaact ccatcctgat aaatggacag tacagcctat agtgctgcca gaaaaggaca   3300
gctggactgt caatgacata cagaaattag tgggaaaatt gaattgggca agtcagattt   3360
atgcagggat taaagtaagg caattatgta aacttcttag gggaaccaaa gcactaacag   3420
aagtagtacc actaacagaa gaagcagagc tagaactggc agaaaacagg gagattctaa   3480
aagaaccggt acatggagtg tattatgacc catcaaaaga cttaatagca gaaatacaga   3540
agcaggggca aggccaatgg acatatcaaa tttatcaaga gccatttaaa aatctgaaaa   3600
caggaaagta tgcaagaatg aagggtgccc acactaatga tgtgaaacaa ttaacagagg   3660
cagtacaaaa aatagccaca gaaagcatag taatatgggg aaagactcct aaatttaaat   3720
tacccataca aaaggaaaca tgggaagcat ggtggacaga gtattggcaa gccacctgga   3780
ttcctgagtg ggagtttgtc aatacccctc ccttagtgaa gttatggtac cagttagaga   3840
aagaacccat aataggagca gaaactttct atgtagatgg ggcagccaat agggaaacta   3900
aattaggaaa agcaggatat gtaactgaca gaggaagaca aaaagttgtc ccctaacgg    3960 acacaacaaa tcagaagact gagttacaag caattcatct agctttgcag gattcgggat   4020
tagaagtaaa catagtgaca gactcacaat atgcattggg aatcattcaa gcacaaccag   4080
ataagagtga atcagagtta gtcagtcaaa taatagagca gttaataaaa aaggaaaaag   4140
tctacctggc atgggtacca gcacacaaag gaattggagg aaatgaacaa gtagataaat   4200
```

```
tggtcagtgc tggaatcagg aaagtactat ttttagatgg aatagataag gcccaagaag    4260
aacatgagaa atatcacagt aattggagag caatggctag tgattttaac ctaccacctg    4320
tagtagcaaa agaaatagta gccagctgtg ataaatgtca gctaaaaggg gaagccatgc    4380
atggacaagt agactgtagc ccaggaatat ggcagctaga ttgtacacat ttagaaggaa    4440
aagttatctt ggtagcagtt catgtagcca gtggatatat agaagcagaa gtaattccag    4500
cagagacagg gcaagaaaca gcatacttcc tcttaaaatt agcaggaaga tggccagtaa    4560
aaacagtaca tacagacaat ggcagcaatt tcaccagtac tacagttaag gccgcctgtt    4620
ggtgggcggg gatcaagcag gaatttggca ttccctacaa tccccaaagt caaggagtaa    4680
tagaatctat gaataaagaa ttaaagaaaa ttataggaca ggtaagagat caggctgaac    4740
atcttaagac agcagtacaa atggcagtat tcatccacaa ttttaaaaga aaggggggga    4800 ttgggggta cagtgcaggg gaaagaatag tagacataat agcaacagac atacaaacta    4860
aagaattaca aaaacaaatt acaaaaattc aaaattttcg ggtttattac agggacagca    4920
gagatccagt ttggaaagga ccagcaaagc tcctctggaa aggtgaaggg gcagtagtaa    4980
tacaagataa tagtgacata aaagtagtgc caagaagaaa agcaaagatc atcagggatt    5040
atggaaaaca gatggcaggt gatgattgtg tggcaagtag acaggatgag gattaacaca    5100
tggaaaagat tagtaaaaca ccatatgtat atttcaagga aagctaagga ctggttttat    5160
agacatcact atgaaagtac taatccaaaa ataagttcag aagtacacat cccactaggg    5220
gatgctaaat tagtaataac aacatattgg ggtctgcata caggagaaag agactggcat    5280
ttgggtcagg gagtctccat agaatggagg aaaaagagat atagcacaca agtagaccct    5340
gacctagcag accaactaat tcatctgcac tattttgatt gtttttcaga atctgctata    5400
agaaatacca tattaggacg tatagttagt cctaggtgtg aatatcaagc aggacataac    5460
aaggtaggat ctctacagta cttggcacta gcagcattaa taaaaccaaa acagataaag    5520
ccacctttgc ctagtgttag gaaactgaca gaggacagat ggaacaagcc ccagaagacc    5580
aagggccaca gagggagcca tacaatgaat ggacactaga gcttttagag gaacttaaga    5640
gtgaagctgt tagacatttt cctaggtata ggctccataa cttaggacaa catatctatg    5700
aaacttacgg ggatacttgg gcaggagtgg aagccataat aagaattctg caacaactgc    5760
tgtttatcca tttcagaatt gggtgtcgac atagcagaat aggcgttact cgacagagga    5820
gagcaagaaa tggagccagt agatcctaga ctagagccct ggaagcatcc aggaagtcag    5880
cctaaaactg cttgtaccaa ttgctattgt aaaaagtgtt gctttcattg ccaagtttgt    5940
ttcatgacaa aagccttagg catctcctat ggcaggaaga agcggagaca cgacgaaga    6000 gctcatcaga acagtcagac tcatcaagct tctctatcaa agcagtaagt agtacatgta    6060
atgcaaccta taatagtagc aatagtagca ttagtagtag caataataat agcaatagtt    6120
gtgtggtcca tagtaatcat agaatatagg aaaatattaa gacaaagaaa aatagacagg    6180
ttaattgata gactaataga aagagcagaa gacagtggca atgagagtga aggagaagta    6240
tcagcacttg tggagatggg ggtggaaatg gggcaccatg ctccttggga tattgatgat    6300
ctgtagtgct acagaaaaat tgtgggtcac agtctattat ggggtacctg tgtggaagga    6360
agcaaccacc actctatttt gtgcatcaga tgctaaagca tatgatacag aggtacataa    6420
tgtttgggcc acacatgcct gtgtacccac agaccccaac ccacaagaag tagtattggt    6480
aaatgtgaca gaaaatttta acatgtggaa aaatgacatg gtagaacaga tgcatgagga    6540
tataatcagt ttatgggatc aaagcctaaa gccatgtgta aaattaaccc cactctgtgt    6600
```

-continued

```
tagtttaaag tgcactgatt tgaagaatga tactaatacc aatagtagta gcgggagaat    6660
gataatggag aaaggagaga taaaaaactg ctctttcaat atcagcacaa gcataagaga    6720
taaggtgcag aaagaatatg cattcttta taaacttgat atagtaccaa tagataatac    6780
cagctatagg ttgataagtt gtaacacctc agtcattaca caggcctgtc caaaggtatc    6840
ctttgagcca attcccatac attattgtgc cccggctggt tttgcgattc taaaatgtaa    6900
taataagacg ttcaatggaa caggaccatg tacaaatgtc agcacagtac aatgtacaca    6960
tggaatcagg ccagtagtat caactcaact gctgttaaat ggcagtctag cagaagaaga    7020
tgtagtaatt agatctgcca atttcacaga caatgctaaa accataatag tacagctgaa    7080
cacatctgta gaaattaatt gtacaagacc caacaacaat acaagaaaaa gtatccgtat    7140
ccagagggga ccaggagag catttgttac aataggaaaa ataggaaata tgagacaagc    7200
acattgtaac attagtagag caaaatggaa tgccacttta aaacagatag ctagcaaatt    7260
aagagaacaa tttggaaata taaaacaat aatctttaag caatcctcag gaggggaccc    7320
agaaattgta acgcacagtt ttaattgtgg aggggaattt ttctactgta attcaacaca    7380 actgttaat agtacttggt ttaatagtac ttggagtact gaagggtcaa ataacactga    7440
aggaagtgac acaatcacac tcccatgcag aataaaacaa tttataaaca tgtggcagga    7500
agtaggaaaa gcaatgtatg cccctcccat cagtggacaa attagatgtt catcaaatat    7560
tactgggctg ctattaacaa gagatggtgg taataacaac aatgggtccg agatcttcag    7620
acctggagga ggcgatatga gggacaattg gagaagtgaa ttatataaat ataaagtagt    7680
aaaaattgaa ccattaggag tagcacccac caaggcaaag agaagagtgg tgcagagaga    7740
aaaaagagca gtgggaatag gagctttgtt ccttgggttc ttgggagcag caggaagcac    7800
tatgggcgca gcgtcaatga cgctgacggt acaggccaga caattattgt ctgatatagt    7860
gcagcagcag aacaatttgc tgagggctat tgaggcgcaa cagcatctgt tgcaactcac    7920
agtctggggc atcaaacagc tccaggcaag aatcctggct gtggaaagat acctaaagga    7980
tcaacagctc ctggggattt ggggttgctc tggaaaactc atttgcacca ctgctgtgcc    8040
ttggaatgct agttggagta aaatctct ggaacagatt tggaataaca tgacctggat    8100
ggagtgggac agagaaatta acaattacac aagcttaata cactccttaa ttgaagaatc    8160
gcaaaaccag caagaaaaga atgaacaaga attattggaa ttagataaat gggcaagttt    8220
gtggaattgg tttaacataa caattggct gtggtatata aaattattca taatgatagt    8280
aggaggcttg gtaggtttaa gaatagtttt tgctgtactt tctatagtga atagagttag    8340
gcagggatat tcaccattat cgtttcagac ccacctccca atcccgaggg gacccgacag    8400
gcccgaagga atagaagaag aaggtggaga gagagcaga gacagatcca ttcgattagt    8460
gaacggatcc ttagcactta tctgggacga tctgcggagc ctgtgcctct tcagctacca    8520
ccgcttgaga gacttactct tgattgtaac gaggattgtg gaacttctgg gacgcagggg    8580
gtgggaagcc ctcaaatatt ggtggaatct cctacagtat tggagtcagg aactaaagaa    8640
tagtgctgtt aacttgctca atgccacagc catagcagta gctgagggga cagatagggt    8700
tatagaagta ttacaagcag cttatagagc tattcgccac atacctagaa gaataagaca    8760
gggcttggaa aggatttgc tataagatgg gtggcaagtg gtcaaaaagt agtgtgattg    8820
gatggcctgc tgtaagggaa agaatgagac gagctgagcc agcagcagat ggggtgggag    8880
cagtatctcg agacctagaa aaacatggag caatcacaag tagcaataca gcagctaaca    8940
atgctgcttg tgcctggcta gaagcacaag aggaggaaga ggtgggtttt ccagtcacac    9000
```

```
ctcaggtacc tttaagacca atgacttaca aggcagctgt agatcttagc cacttttaa    9060 aagaaaaggg gggactggaa gggctaattc actcccaaag aagacaagat atccttgatc    9120
tgtggatcta ccacacacaa ggctacttcc ctgattggca gaactacaca ccagggccag    9180
gggtcagata tccactgacc tttggatggt gctacaagct agtaccagtt gagccagata    9240
aggtagaaga ggccaataaa ggagagaaca ccagcttgtt acaccctgtg agcctgcatg    9300
gaatggatga ccctgagaga gaagtgttag agtggaggtt tgacagccgc ctagcatttc    9360
atcacgtggc ccgagagctg catccggagt acttcaagaa ctgctgacat cgagcttgct    9420
acaagggact ttccgctggg acttttccag ggaggcgtgg cctgggcggg actggggagt    9480
ggcgagccct cagatgctgc atataagcag ctgctttttg cctgtactgg gtctctctgg    9540
ttagaccaga tctgagcctg ggagctctct ggctaactag ggaacccact gcttaagcct    9600
caataaagct tgccttgagt gcttcaagta gtgtgtgccc gtctgttgtg tgactctggt    9660
aactagagat ccctcagacc cttttagtca gtgtggaaaa tctctagcac ccaggaggta    9720
gaggttgcag tgagccaaga tcgcgccact gcattccagc ctgggcaaga aaacaagact    9780
gtctaaaata ataataataa gttaagggta ttaaatatat ttatacatgg aggtcataaa    9840
aatatatata tttgggctgg gcgcagtggc tcacacctgc gcccggccct ttgggaggcc    9900
gaggcaggtg gatcacctga gtttgggagt tccagaccag cctgaccaac atggagaaac    9960
cccttctctg tgtatttta gtagatttta ttttatgtgt attttattca caggtatttc    10020
tggaaaactg aaactgtttt cctctactc tgataccaca agaatcatca gcacagagga    10080
agacttctgt gatcaaatgt ggtgggagag ggaggtttc accagcacat gagcagtcag    10140
ttctgccgca gactcggcgg gtgtccttcg gttcagttcc aacaccgcct gcctggagag    10200
aggtcagacc acagggtgag ggctcagtcc ccaagacata acacccaag acataaacac    10260 ccaacaggtc caccccgcct gctgcccagg cagagccgat tcaccaagac gggaattagg    10320
atagagaaag agtaagtcac acagagccgg ctgtgcggga aacggagtt ctattatgac    10380 tcaaatcagt ctcccccaagc attcggggat cagagttttt aaggataact tagtgtgtag    10440
ggggccagtg agttggagat gaaagcgtag ggagtcgaag gtgtcctttt gcgccgagtc    10500
agttcctggg tgggggccac aagatcggat gagccagttt atcaatccgg gggtgccagc    10560
tgatccatgg agtgcaggt ctgcaaaata tctcaagcac tgattgatct taggttttac    10620
aatagtgatg ttaccccagg aacaatttgg ggaaggtcag aatcttgtag cctgtagctg    10680
catgactcct aaaccataat ttcttttttg tttttttttt tttattttg agacagggtc    10740 tcactctgtc acctaggctg gagtgcagtg gtgcaatcac agctcactgc agcctcaacg    10800
tcgtaagctc aagcgatcct cccacctcag cctgcctggt agctgagact acaagcgacg    10860
ccccagttaa tttttgtatt tttggtagag gcagcgtttt gccgtgtggc cctggctggt    10920
ctcgaactcc tgggctcaag tgatccagcc tcagcctccc aaagtgctgg gacaaccggg    10980
gccagtcact gcacctggcc ctaaaccata atttctaatc ttttggctaa tttgttagtc    11040
ctacaaaggc agtctagtcc ccaggcaaaa aggggggtttg tttcgggaaa gggctgttac    11100
tgtctttgtt tcaaactata aactaagttc ctcctaaact tagttcggcc tacacccagg    11160
aatgaacaag gagagcttgg aggttagaag cacgatggaa ttggttaggt cagatctctt    11220
tcactgtctg agttataatt ttgcaatggt ggttcaaaga ctgcccgctt ctgacaccag    11280
tcgctgcatt aatgaatcgg ccaacgcgcg gggagaggcg gtttgcgtat tgggcgctct    11340
tccgcttcct cgctcactga ctcgctgcgc tcggtcgttc ggctgcggcg agcggtatca    11400
```

```
gctcactcaa aggcggtaat acggttatcc acagaatcag gggataacgc aggaaagaac    11460
atgtgagcaa aaggccagca aaaggccagg aaccgtaaaa aggccgcgtt gctggcgttt    11520
ttccataggc tccgccccc  tgacgagcat cacaaaaatc gacgctcaag tcagaggtgg    11580
cgaaacccga caggactata aagataccag gcgtttcccc ctggaagctc cctcgtgcgc    11640
tctcctgttc cgaccctgcc gcttaccgga tacctgtccg cctttctccc ttcgggaagc    11700
gtggcgcttt ctcatagctc acgctgtagg tatctcagtt cggtgtaggt cgttcgctcc    11760
aagctgggct gtgtgcacga acccccgtt  cagcccgacc gctgcgcctt atccggtaac    11820
tatcgtcttg agtccaaccc ggtaagacac gacttatcgc cactggcagc agccactggt    11880
aacaggatta gcagagcgag gtatgtaggc ggtgctacag agttcttgaa gtggtggcct    11940
aactacggct acactagaag aacagtattt ggtatctgcg ctctgctgaa gccagttacc    12000
ttcggaaaaa gagttggtag ctcttgatcc ggcaaacaaa ccaccgctgg tagcggtggt    12060
ttttttgttt gcaagcagca gattacgcgc agaaaaaaag gatctcaaga agatcctttg    12120
atcttttcta cggggtctga cgctcagtgg aacgaaaact cacgttaagg gattttggtc    12180
atgagattat caaaaaggat cttcacctag atccttttaa attaaaaatg aagttttaaa    12240
tcaatctaaa gtatatatga gtaaacttgg tctgacagtt accaatgctt aatcagtgag    12300
gcacctatct cagcgatctg tctatttcgt tcatccatag ttgcctgact ccccgtcgtg    12360
tagataacta cgatacggga gggcttacca tctggcccca gtgctgcaat gataccgcga    12420
gacccacgct caccggctcc agatttatca gcaataaacc agccagccgg aagggccgag    12480
cgcagaagtg gtcctgcaac tttatccgcc tccatccagt ctattaattg ttgccgggaa    12540
gctagagtaa gtagttcgcc agttaatagt ttgcgcaacg ttgttgccat tgctacaggc    12600
atcgtggtgt cacgctcgtc gtttggtatg gcttcattca gctccggttc caacgatca    12660 aggcgagtta catgatcccc catgttgtgc aaaaaagcgg ttagctcctt cggtcctccg    12720
atcgttgtca gaagtaagtt ggccgcagtg ttatcactca tggttatggc agcactgcat    12780
aattctctta ctgtcatgcc atccgtaaga tgcttttctg tgactggtga gtactcaacc    12840
aagtcattct gagaatagtg tatgcggcga ccgagttgct cttgcccggc gtcaatacgg    12900
gataataccg cgccacatag cagaacttta aaagtgctca tcattggaaa acgttcttcg    12960
gggcgaaaac tctcaaggat cttaccgctg ttgagatcca gttcgatgta acccactcgt    13020
gcacccaact gatcttcagc atcttttact ttcaccagcg tttctgggtg agcaaaaaca    13080
ggaaggcaaa atgccgcaaa aaagggaata agggcgacac ggaaatgttg aatactcata    13140
ctcttccttt ttcaatatta ttgaagcatt tatcagggtt attgtctcat gagcggatac    13200
atatttgaat gtatttagaa aaataaacaa ataggggttc cgcgcacatt tccccgaaaa    13260
gtgccacctg acgtctaaga aaccattatt atcatgacat taacctataa aaataggcgt    13320
atcacgaggc cctttcgtct cgcgcgtttc ggtgatgacg gtgaaaacct ctgacacatg    13380
cagctcccgg agacggtcac agcttgtctg taagcggatg ccgggagcag acaagcccgt    13440
cagggcgcgt cagcgggtgt tggcgggtgt cggggctggc ttaactatgc ggcatcagag    13500
cagattgtac tgagagtgca ccatatgcgg tgtgaaatac cgcacagatg cgtaaggaga    13560
aaataccgca tcaggcgcca ttcgccattc aggctgcgca actgttggga agggcgatcg    13620
gtgcgggcct cttcgctatt acgccagggg aggcagagat tgcagtaagc tgagatcgca    13680
gcactgcact ccagcctggg cgacagagta agactctgtc tcaaaaataa aataaataaa    13740
tcaatcagat attccaatct tttccttttat ttatttattt attttctatt ttggaaacac    13800
```

```
agtccttcct tattccagaa ttacacatat attctatttt tctttatatg ctccagtttt   13860
ttttagacct tcacctgaaa tgtgtgtata caaaatctag gccagtccag cagagcctaa   13920
aggtaaaaaa taaaataata aaaataaat aaaatctagc tcactccttc acatcaaaat    13980
ggagatacag ctgttagcat taaataccaa ataacccatc ttgtcctcaa taattttaag   14040
cgcctctctc caccacatct aactcctgtc aaaggcatgt gccccttccg ggcgctctgc   14100
tgtgctgcca accaactggc atgtggactc tgcagggtcc ctaactgcca agccccacag   14160
tgtgccctga ggctgccct tccttctagc ggctgccccc actcggcttt gctttcccta    14220
gtttcagtta cttgcgttca gccaaggtct gaaactaggt gcgcacagag cggtaagact   14280
gcgagagaaa gagaccagct ttacaggggg tttatcacag tgcaccctga cagtcgtcag   14340
cctcacaggg ggtttatcac attgcaccct gacagtcgtc agcctcacag ggggtttatc   14400
acagtgcacc cttacaatca ttccatttga ttcacaattt ttttagtctc tactgtgcct   14460
aacttgtaag ttaaatttga tcagaggtgt gttcccagag gggaaaacag tatatacagg   14520
gttcagtact atcgcatttc aggcctccac ctgggtcttg gaatgtgtcc cccgaggggt   14580
gatgactacc tcagttggat ctccacaggt cacagtgaca caagataacc aagacacctc   14640
ccaaggctac cacaatgggc cgccctccac gtgcacatgg ccggaggaac tgccatgtcg   14700
gaggtgcaag cacacctgcg catcagagtc cttggtgtgg agggagggac cagcgcagct   14760
tccagccatc cacctgatga acagaaccta gggaaagccc cagttctact tacaccagga   14820
aaggc                                                               14825
```

<210> SEQ ID NO 3
<211> LENGTH: 305
<212> TYPE: PRT
<213> ORGANISM: Artificial Sequence
<220> FEATURE:
<223> OTHER INFORMATION: Reverse transcriptase from NL4-3 HIV

<400> SEQUENCE: 3

```
Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Val Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Gln Lys Lys Ser Val Thr Val Leu Asp Val Gly
            100                 105                 110

Asp Ala Tyr Phe Ser Val Pro Leu Asp Lys Asp Phe Arg Lys Tyr Thr
        115                 120                 125

Ala Phe Thr Ile Pro Ser Ile Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Cys Ser Met Thr Lys Ile Leu Glu Pro Phe Arg Lys Gln Asn Pro
                165                 170                 175
```

```
Asp Ile Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Gln His
            195                 200                 205

Leu Leu Arg Trp Gly Phe Thr Thr Pro Asp Lys Lys His Gln Lys Glu
            210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
            245                 250                 255

Ile Gln Lys Leu Val Gly Lys Leu Asn Trp Ala Ser Gln Ile Tyr Ala
            260                 265                 270

Gly Ile Lys Val Arg Gln Leu Cys Lys Leu Leu Arg Gly Thr Lys Ala
            275                 280                 285

Leu Thr Glu Val Val Pro Leu Thr Glu Glu Ala Glu Leu Glu Leu Ala
            290                 295                 300

Glu
305

<210> SEQ ID NO 4
<211> LENGTH: 99
<212> TYPE: PRT
<213> ORGANISM: Artificial Sequence
<220> FEATURE:
<223> OTHER INFORMATION: Protease from NL4-3 HIV

<400> SEQUENCE: 4

Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
            35                  40                  45

Gly Ile Gly Gly Phe Ile Lys Val Arg Gln Tyr Asp Gln Ile Leu Ile
        50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe
```